(12) United States Patent
Ikezono et al.

(10) Patent No.: US 7,863,005 B2
(45) Date of Patent: Jan. 4, 2011

(54) METHOD FOR DETECTING PERILYMPHATIC FISTULA

(75) Inventors: Tetsuo Ikezono, Tokyo (JP); Toshiaki Yagi, Tokyo (JP); Akira Omori, Kanagawa (JP)

(73) Assignee: Nippon Medical School Foundation, Tokyo (JP)

( * ) Notice: Subject to any disclaimer, the term of this patent is extended or adjusted under 35 U.S.C. 154(b) by 772 days.

(21) Appl. No.: 10/517,778

(22) PCT Filed: Jun. 26, 2003

(86) PCT No.: PCT/JP03/08123

§ 371 (c)(1),
(2), (4) Date: Apr. 14, 2006

(87) PCT Pub. No.: WO2004/003020

PCT Pub. Date: Jan. 8, 2004

(65) Prior Publication Data

US 2006/0246516 A1    Nov. 2, 2006

(30) Foreign Application Priority Data

Jun. 27, 2002    (JP) ............................. 2002-187479

(51) Int. Cl.
*G01N 33/53* (2006.01)
*C07K 16/18* (2006.01)
(52) U.S. Cl. .......................................... 435/7.1; 435/4
(58) Field of Classification Search ...................... None
See application file for complete search history.

(56) References Cited

U.S. PATENT DOCUMENTS

| | | | |
|---|---|---|---|
| 4,830,024 A | | 5/1989 | Nashner et al. |
| 6,274,554 B1 * | | 8/2001 | Magal et al. ................... 514/12 |
| 6,730,475 B1 | | 5/2004 | Robertson et al. |
| 6,913,919 B2 * | | 7/2005 | Botstein et al. .......... 435/252.3 |
| 2002/0004228 A1 | | 1/2002 | Holloway |
| 2003/0082646 A1 * | | 5/2003 | Carey et al. ................ 435/7.21 |

FOREIGN PATENT DOCUMENTS

WO    00/71081    11/2000

OTHER PUBLICATIONS

Dictionary of Medicine, definition for the term "perilymph" (2000); Peter Collin Publishing, London: Peter Collin Publishing. Retrieved Oct. 21, 2008, from http://www.credoreference.com/entry/1051726/.*
Wall et al. "Perilymph fistula pathophysiology" Otolaryngol Head Neck Surg. Jan. 1995;112(1):145-53.*
Wolfe, S.L., Molecular and Cellular Biology, 1993, pp. 790-793.*
The Academic Press Dictionary of Science and Technology, definition for the term "polyclonal" (1996) Oxford: Elsevier Science & Technology. Retrieved Oct. 22, 2008, from http://www.credoreference.com/entry/3144515/.*
Ilkezono et al. "Cochlin-Tomoprotein: A Novel Perilymph-Specific Protein and a Potential Marker for the Diagnosis of Perilymphatic Fistula" Audiol Neurotol 2009;14:338-344.*
Ikezono et al. "Identification of a novel Cochlin isoform in the perilymph: insights to Cochlin function and the pathogenesis of DFNA9" Biochemical and Biophysical Research Communications 314 (2004) 440-446.*
Y. Asano et al., Prospects of Otolaryngology, 1991, vol. 34, No. 4, pp. 411-425, along with an English Language Summary.
K. Yoshioka, Prospects of Otolaryngology, 1983, vol. 26, Suppl. 6, pp. 517-539, along with an English Language Summary.
D.C. Fitzgerald, Ann. Otol. Rhinol. Laryngol., 2001, vol. 110, pp. 430-436.
I. Thalmann et al., Otolaryngology—Head and Neck Surgery, 1994, vol. 111, No. 3, pp. 273-280.
H. Kanzaki et al., "Koserodosho tokutei sikkan taisaku kenkyu jigyokyusei kodo kanon nancho ni kansuru cyosa kenkyu han/heisei 11 nendo hokokusho (Annual report 1999, by the Research project team regarding acute profound sensorineural hearingloss, Research project for specified diseases, the Ministry of Health, Labour and Welfare)", 2000, pp. 41-41.
G. Bachmann et al., The Journal of Laryngology & Otology, 2001, vol. 115, pp. 132-135.
S.D. Rauch, The Laryngoscope, 2000, vol. 110, No. 4, pp. 545-552.
N.G. Robertson et al., Nature Genetics, 1998, vol. 20, pp. 299-303.
NCBI OMIM, http://www.ncbi.nlm.nih.gov., Cochlin Coch5B2, 2005, 5 pages.
M. Trexler et al., Eur. J. Biochem., 2000, vol. 267, pp. 5751-5757.
T. Ikezono et al., Biochimica et Biophysica Acta, 2001, vol. 1535, pp. 258-265.
N.G. Robertson, Hum. Mol. Genet., 2001, vol. 10, No. 22, pp. 2493-2500.
G. Kohler et al., Nature, 1975, vol. 256, pp. 495-497.
S. Shindo et al., "Cochlin Kanren Tanpaku o mochiita Kai-Lymph-ro Shindan no Kokoromi", Dai 104 kai The Oto-Rhino-Laryngological Society of Japan, Inc., Sokai Gakujutsu Koenkai Yokoshu, vol. 106, No. 4, p. 106, Abstract #132 (2003).
N. Robertson et al., "Subcellular Localisation, Secretion, and Post-Translational Processing of Normal Cochlin, and of Mutants Causing the Sensorineural Deafness and Vestibular Disorder, DFNA9", J. Med. Genet., vol. 40 pp. 479-486 (2003).

* cited by examiner

*Primary Examiner*—Mark L Shibuya
*Assistant Examiner*—Christine Foster
(74) *Attorney, Agent, or Firm*—Greenblum & Bernstein, P.L.C.

(57) ABSTRACT

It is an object of the present invention to provide a simple, reliable and low-invasive method to detect perilymph fistulas. The present invention provides a method for detecting a perilymph fistula, which comprises detecting the existence of Cochlin in body fluid existing in the middle ear.

3 Claims, 10 Drawing Sheets

```
        1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0
  0     M S A A W I P A L G L G V C L L L L P G P A G S E G A A P I A I T C F T R G L D I R K E K A D V L C
                                                      ⇒63                36—50 (anti LCCL antibody)

1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0
 50     P G G C P L E E F S V Y G N I V Y A S V S S I C G A A V H R G V I S N S G G P V R V Y S L P G R E N
                            63–83 (anti LCCL 1 antibody)                                   95–111

1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0
100     Y S S V D A N G I Q S Q M L S R W S A S F T V T K G K S S T Q E A T G Q A V S T A H P P T G K R L K
          (anti LCCL 2 antibody)           114–127  (anti LCCL 3 antibody)     ⇒p44   137–151 (anti p63/44 antibody)

1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0
150     K T P E K K T G N K D C K A D I A F L I D G S F N I G Q R R F N L Q K N F V G K V A L M L G I G T E
        ⇒p40                              163–181  (anti p63/44/40 antibody)

1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0
200     G P H V G L V Q A S E H P K I E F Y L K N F T S A K D V L F A I K E V G F R G G N S N T G K A L K H
```

METHOD FOR DETECTING PERILYMPHATIC FISTULA

TECHNICAL FIELD

The present invention relates to a method for detecting perilymph fistulas, and an antibody, a reagent, and a kit, which are used in such detection.

BACKGROUND ART

A perilymph fistula is a disorder of the auditory and vestibular system, which is caused by leakage of the perilymph existing in the inner ear tissues into the tympanic cavity (middle ear) through the inner ear windows (through either the round or oval window, or though both the round and oval windows), or through the fissura ante fenestram (which is a bone fissure located between the inner ear and the middle ear). Causes of this disease are considered to be congenital malformation, syphilis, stapes surgery, head injury (including barotraumas), sudden development (cryptogenic development), and the like. It has been known that perilymph fistulas are also caused by a drastic change in cerebrospinal fluid pressure or inner ear pressure, which is generated as a result of ordinary actions in our daily life, such as nose-blowing, sneezing, coughing, muscle straining, diving, climbing, or experiencing head trauma. This is a disease involving partial acute sensorineural deafness, vertigo, or disorder of balance.

Diagnosis of perilymph fistulas has conventionally been carried out by a method of comprehensively verifying physiological findings, symptoms, history of diseases, and other factors, in accordance with diagnostic standards (Asano et al., "*Jiten* (Prospects of Otolaryngology)" 34, 4; 1991, pp. 411-425). Accordingly, in many cases, the diagnosis is uncertain, and exploratory tympanotomy selected as a means for obtaining definite diagnosis has been problematic in terms of invasiveness to the patients. Moreover, there have been many cases where perilymph leakage cannot be confirmed by visual observation even when such exploratory tympanotomy is carried out, thereby resulting in a lack of definite diagnosis.

Sudden deafness is a type of acute sensorineural hearingloss, the cause of which cannot be specified, and it is a disease representing the highest percentage of instance among the various types of acute sensorineural hearingloss. It has been reported that as a result of tentatively performing exploratory tympanotomy on patients with sudden deafness, perilymph fistulas were observed in 8 out of 11 cases (Kunihide Yoshioka, "*Jibiinkoka Tenbo* (Prospects of Otolaryngology)," Vol. 26, Suppl. 6; 1983: pp. 517-539). Moreover, it has also been known that some patients with perilymph fistulas are misdaignosed as Meniere's disease, which is known as one cause of acute sensorineural hearingloss, and regarding which the number of the patients has increased in modern society. A report emphasizes the differential diagnosis between perilymph fistula an Meniere's disease based on the analysis of a large number of patients with this affliction. (D. C. Fitzgerald, "Ann. Otol. Rhinol. Laryngol." 110; 2001: pp. 430-436). These facts show that perilymph fistulas are misdiagnosed as other diseases because the symptoms do not comply with the aforementioned diagnostic criteria. However, since a method for definite diagnosis of perilymph fistulas has not been established yet, the real picture is that it is still difficult to substantially identify the disease in the clinical setting. Thus, these problems have not yet been solved. Among various types of acute sensorineural hearingloss, the perilymph fistula is the only disease where disorders of the auditory and vestiblar system can be improved by operations, and prompt treatment greatly influences the cure rate thereof. Accordingly, it is strongly desired that a simple, reliable and low-invasive test for the diagnosis of perilymph fistulas to be developed.

To date, the following reports have been made: a report that proposes searching for a marker that can be used in diagnosis of perilymph fistulas and using ApoD and ApoJ as indicators (Thalmann et al., "Otolaryngology—Head and Neck Surgery," 111, 3, 1; 1994: pp. 273-280); a report regarding an attempt to diagnose perilymph fistulas using GM1 (monosialoganglioside 1) as an indicator (Hitoshi Kanzaki et al., "*Koseirodosho tokutei sikkan taisaku kenkyu jigyo/Kyusei kodo kanon nancho ni kansuru cyosa kenkyu han/Heisei* 11 *nendo hokokusho* (Annual report 1999, by the Research project team regarding acute profound sensorineural hearingloss, Research project for specified diseases, the Ministry of Health, Labour and Welfare)," 2000: pp. 41-43); a report that proposes the use of prostagrandin D synthase as an indicator (G. Bachmann, et al., "J. Laryngol. Otol." 115; 2001: pp. 132-135); a report regarding an attempt to diagnose perilymph fistulas using transferrin as an indicator (Rauch S. D., "Laryngoscope" 110(4); 2000: pp. 545-552); and so on. However, these techniques are not good enough for clinical applications.

COCH is a gene that has been identified as a causative gene of non-syndromic hereditary hearingloss DFNA9. A COCH protein encoded by this gene was designated "Cochlin" (N. G. Robertson, "Nature Genet." 20; 1998, pp. 299-303; and NCBI OMIM home page, www.ncbi.nlm.nih.gov.

Focusing attention on the fact that Cochlin is an important protein with reference to human deafness, the present inventors have conducted a proteome analysis of Cochlin in bovine inner ear tissues, and have clarified that Cochlin has 3 different N-termini and that Cochlin exists as 3 types of isoforms, p63, p44, and p40, having molecular weights of 63 kDa, 44 kDa, and 40 kDa, respectively. In addition, the present inventors have reported that the LCCL module exists at the N-terminus (Trexler et al., "Eur. J. Biochem." 267; 2000: pp. 5751-5757), that all mutations that have been discovered so far regarding DFNA9 are presented in this module, and that the mutations are contained only in the isoform p63, but not contained in the other isoforms (Ikezono et al., "Biochem. Biophys. Acta" 1535(3); 2001: pp. 258-265). However, with regard to the above report, a proteome analysis was only carried out via two-dimensional gel electrophoresis (2D-GE) on bovine inner ear tissues, and the clinical significance of Cochlin and the like has not been sufficiently studied.

N. G. Robertson et al. have produced an antibody to Cochlin, and have carried out immunological staining of inner ear tissues, so as to analyze the expression of Cochlin in the inner ear tissues (N. G. Robertson, "Hum. Mol. Genet." 10(22): 2001: pp. 2493-2500). However, this report only describes analyses regarding localization of the protein in inner ear tissues or the like, and thus, there have been no findings regarding the existence of Cochlin in the perilymph.

DISCLOSURE OF THE INVENTION

It is an object of the present invention to provide a simple, reliable and low-invasive method to detect perilymph fistulas. It is another object of the present invention to provide an antibody, a reagent, and a kit, which are used for the above detection method of the present invention.

As a result of intensive studies directed towards achieving the aforementioned objects, the present inventors have found that perilymph fistulas can be detected by using, as a sample, body fluid existing in the middle ear of a patient likely to have a perilymph fistula, and using the existence of Cochlin in the sample as an indicator. The present invention has been made based on these findings.

That is to say, the present invention provides the following features.

(1) A method for detecting a perilymph fistula, which comprises detecting the existence of Cochlin in body fluid existing in the middle ear.
(2) The method according to (1) above, which comprises detecting the existence of Cochlin in body fluid existing in the middle ear of a patient likely to have a perilymph fistula, and using the detected existence of Cochlin as an indicator of the possibility of a perilymph fistula.
(3) The method according to (1) or (2) above, wherein the detection of the existence of Cochlin is carried out by detecting the existence of a protein consisting of the N-terminal fragment of Cochlin.
(4) The method according to any one of (1) to (3) above, wherein the existence of Cochlin is detected by an immunological method.
(5) The method according to (4) above, wherein the immunological method is carried out using an anti-Cochlin N-terminal fragment antibody.
(6) The method according to (4) or (5) above, wherein the immunological method is carried out by using an antibody which recognizes an antigenic determinant contained in an amino acid sequence portion corresponding to amino acids at positions 36 to 127 of the amino acid sequence shown in SEQ ID NO: 1 of the sequence listing.
(7) The method according to any one of (4) to (6) above, wherein the immunological method is carried out by using an anti-Cochlin N-terminal fragment antibody characterized in that it recognizes an antigenic determinant contained in a polypeptide having the amino acid sequence shown in SEQ ID NO: 2, 5, 6, or 7 of the sequence listing.
(8) An anti-Cochlin N-terminal fragment antibody, which is characterized in that it recognizes an antigenic determinant contained in a polypeptide having the amino acid sequence shown in SEQ ID NO: 2, 5, 6, or 7 of the sequence listing.
(9) A reagent for detection of a perilymph fistula, which comprises an anti-Cochlin antibody.
(10) The reagent for detection of a perilymph fistula according to (9) above, wherein the anti-Cochlin antibody is an anti-Cochlin N-terminal fragment antibody.
(11) The reagent for detection of a perilymph fistula according to (9) or (10) above, wherein the anti-Cochlin antibody recognizes an antigenic determinant contained in an amino acid sequence portion corresponding to amino acids at positions 36 to 127 of the amino acid sequence shown in SEQ ID NO: 1 of the sequence listing.
(12) The reagent for detection of a perilymph fistula according to any one of (9) to (11) above, wherein the anti-Cochlin antibody is an anti-Cochlin N-terminal fragment antibody characterized in that it recognizes an antigenic determinant contained in a polypeptide having the amino acid sequence shown in SEQ ID NO: 2, 5, 6, or 7 of the sequence listing.
(13) A reagent kit for detection of a perilymph fistula, which comprises the reagent of detection of a perilymph fistula according to any one of (9) to (12) above.

BRIEF DESCRIPTION OF THE DRAWINGS

FIG. 10 shows the positional relationship of antigen polypeptides used to prepare the antibody of the present invention on amino acids 1-250 of the sequence shown in SEQ ID NO: 1.

BEST MODE FOR CARRYING OUT THE INVENTION

Figure 1:
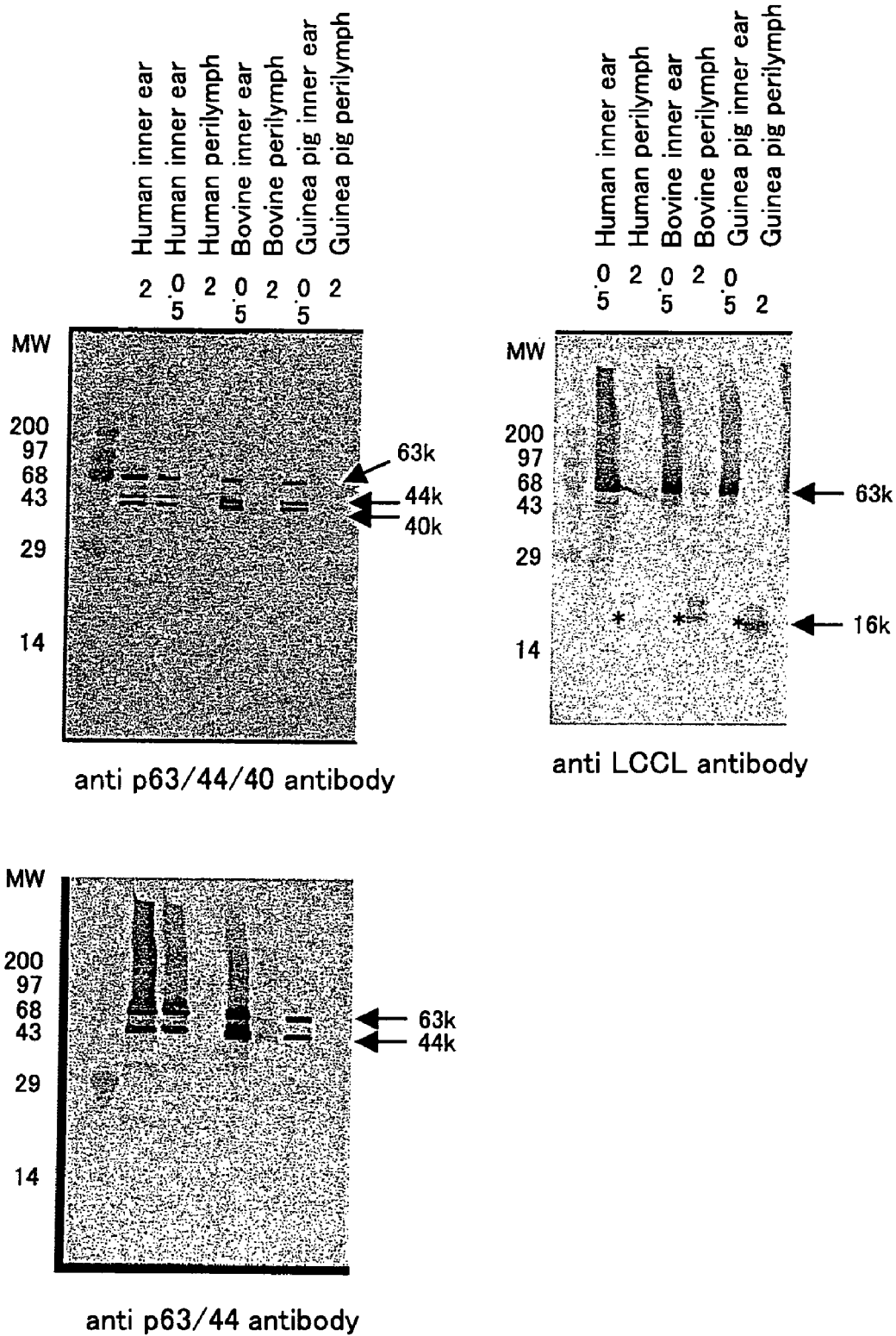
FIG. 1 shows the results obtained by analyzing the inner ear tissue extracts and perilymphs of a human, a bovine, and a guinea pig, by Western blot, using 3 types of antibodies: an anti-p63/44/40 antibody, an anti-p63/44 antibody, and an anti-LCCL antibody.

The embodiments of the present invention will be described further in detail below.

In the present specification, techniques such as purification and analysis of proteins and preparation of antibodies can be carried out according to the methods described in general experiment manuals such as *Shin Seikagaku Jikken Koza* (New Biochemical Experiment Courses) (edited by the Japanese Biochemical Society; Tokyo Kagaku Dojin Co., Ltd.), or Antibodies—A Laboratory Manual (E. Harlow, et al., Cold Spring Harbor Laboratory (1988)); or methods equivalent thereto, unless otherwise specified.

1. A Method for Detecting Perilymph Fistulas

In the present invention, a perilymph fistula is a disorder of the auditory and vestiblar system, which is caused by leakage of the perilymph existing in the inner ear tissues into the tympanic cavity (middle ear) through the inner ear window (through either the round or oval window, or though both the round and oval windows), or through the fissura ante fenestram (which is a bone fissure located between the inner ear and the middle ear) due to a certain factor. This disease can be detected by confirming the leakage of perilymph into the middle ear. The method of detection of a perilymph fistula of the present invention is characterized in that the existence of Cochlin in the perilymph only, among body fluids that can exist in the middle ear of a patient likely to have the disease, is detected, and such detection is used as an indicator for the possibility that the patient suffers from a perilymph fistula. According to the present method, detection can be carried out regardless of factors contributing to the development of perilymph fistulas or mechanisms of the disease.

Cochlin is a protein encoded by a COCH gene, which has been identified as a causative gene of non-syndromic hereditary hearingloss DFNA9 (N. G. Robertson, Nature Genet., 20, 299-303 (1998)). This protein has 3 different N-termini in mammals such as humans, bovines, guinea pigs, or rats, and the protein exist as 3 types of isoforms, p63, p44, and p40, having molecular weights of 63 kDa, 44 kDa, and 40 kDa, respectively (Ikezono et al., Biochem. Biophys. Acta, 1535, 3, 258-265 (2001)). In the present specification, the amino acid sequence of Cochlin shown in SEQ ID NO: 1 in the sequence listing is the amino acid sequence of human Cochlin described in Nature Genet., 20, 299-303 (1998). Thus, amino acid numbers used in the present specification correspond to those in the above amino acid sequence. For example, the isoform p63 having a molecular weight of 63 kDa, which is the largest Cochlin isoform in humans, is a protein having an amino acid sequence portion corresponding to amino acids at positions 25 to 550 of the above amino acid sequence. The isoform p44 is a protein having an amino acid sequence portion corresponding to amino acids at positions 133 to 550 thereof, and the isoform p40 is a protein having an amino acid sequence portion corresponding to amino acids at positions 152 to 550 thereof. In addition, a portion corresponding to amino acids at positions 1 to 24 of the above amino acid sequence is a signal sequence.

In the present invention, as Cochlin used as an indicator of the possibility of the development of a perilymph fistula, a protein comprising a fragment having the amino acid sequence of the N-terminus of the isoform p63 (hereinafter referred to as an "N-terminal fragment" at times) is preferably used. Any protein may be used as such a fragment regardless of size, as long as it has the amino acid sequence of the N-terminus of the isoform p63 of Cochlin. An example of such a fragment is a fragment having an amino acid sequence portion corresponding to amino acids at positions 36 to 127 of the amino acid sequence shown in SEQ ID NO: 1. Among others, a more preferred example is an N-terminal fragment having a molecular weight of approximately 16 kDa, which is recognized by an anti-Cochlin N-terminal fragment antibody, characterized in that the antibody recognizes an antigenic determinant contained in a polypeptide having the amino acid sequence shown in SEQ ID NO: 2, 5, 6, or 7, which will be described later. In particular, a particularly preferred example is an N-terminal fragment having a molecular weight of approximately 16 kDa, which is recognized by an antibody or the like, characterized in that it recognizes an antigenic determinant contained in a polypeptide having the amino acid sequence shown in SEQ ID NOS: 2 and/or 7. In addition, other than the aforementioned fragments, any proteins having the amino acid sequence shown in SEQ ID NO: 1 of the sequence listing or a partial sequence thereof can be used, as long as they do not substantially exist in other body fluids that can exist in the middle ear of a human, but exist in the perilymph only. More specifically, the isoform p63, p44, or p40 may be used. Further, proteins comprising fragments thereof or the like may also be used. In the present specification, the aforementioned proteins may be simply referred to as "Cochlin". It is to be noted that all the molecular weights (kDa) of the aforementioned 3 isoforms and N-terminal fragments of Cochlin were calculated by calibration by two-dimensional electrophoresis, using a size marker.

A body fluid existing in the middle ear of a patient likely to have a perilymph fistula is used as a sample subjected to the detection method of the present invention. Examples of a body fluid that can exist in the middle ear of a human may include perilymph, cerebro-spinal fluid (hereinafter referred to as "CSF" at times), blood, saliva, and middle ear mucus produced from the middle ear mucous membrane. In the case of CSF, for example, it has been known that CSF flows into the inner ear through the eighth cranial nerve pathway or cochlear aqueduct of the internal acoustic meatus due to operations or the like, and then flows into the middle ear, and that CSF also flows into the middle ear due to experiencing head trauma or fracture, malformation of the inner ear, etc. The blood may exist in the middle ear as a result of bleeding due to head trauma, bleeding from the middle ear mucosa, or the like. It has been known that the saliva may exist in the middle ear as a result of backflow of the saliva existing in the epipharynx through the Eustachian tube. In addition, patients with otitis media with effusion may have a middle ear exudate, and patients with chronic otitis media may have otorrhea (pus). These body fluids cannot be distinguished by visual observation. However, these are collected and subjected to analysis, and thus, the existence of Cochlin in the sample is analyzed, so that it is possible to determine whether or not the collected body fluid is the perilymph, and so that it can be used as an indicator of the possibility of the development of a perilymph fistula.

Any method may be used as a method of collecting a body fluid existing in the middle ear, as long as it is a method capable of collecting a body fluid without allowing the blood, agent, or the like to mix into the body fluid, and also without allowing other proteins or the like to mix therein, while involving low invasiveness for patients. For example, a very small portion of the tympanic membrane may be excised, a syringe or the like may be inserted into such a portion, and a body fluid existing therein may be drawn and collected. Alternatively, such a body fluid may be collected by inserting a cotton-tipped swab to wipe the body fluid. When a body fluid to be collected exists in a trace amount, a method is preferably used that comprises injecting an appropriate amount of a suitable solution, such as a saline solution, into the portion, using a syringe or the like, and recovering the body fluid contained in the above solution using a syringe or the like. In the present invention, a solution recovered by such a method is referred to as a "middle ear lavarge." As a solution used herein, a solution that is physiologically acceptable in terms of composition, pH, temperature, and other factors, and does not cause undue burden for patients, is selected. Moreover, since the middle ear is connected with the epipharynx and the mesopharynx via the auditory tube, a body fluid derived from the middle ear that reaches the epipharynx or mesopharynx via the auditory tube may also be collected. More specifically, for example, a cotton-tipped swab or the like may be inserted from the oral cavity or nasal cavity, and a body fluid existing in the epipharynx or mesopharynx may be collected by wiping it.

Immediately after collection, the thus collected body fluid is preferably subjected to analysis. However, it is also possible to conserve it under low temperature conditions, such as at a temperature between 4° C. and −80° C., and preferably between −20° C. and −70° C. To conserve the collected body fluid, a preservative agent for suppressing denaturation of proteins, or an antiseptic agent for preventing putrefaction, may be added, as necessary. In addition, these samples may be subjected to pretreatment such as concentration or purification before analysis, as necessary. As specific means, commonly used means, such as known concentration or purification means for proteins, may be used.

As a method for detecting the existence of Cochlin in a body fluid existing in the middle ear of a patient likely to have a perilymph fistula, which is collected by the above-described method, any method can be applied as long as it is a known method of detecting and analyzing proteins. More specifically, the existence of Cochlin may be detected by either an immunological or non-immunological method (liquid chromatography, two-dimensional electrophoresis, mass spectrometry, a combination thereof, etc.). Of these, an immunological method of using an antibody which recognizes the above Cochlin or a partial polypeptide thereof (hereinafter referred to as an "anti-Cochlin antibody" at times) is preferably used in the present invention. Any method can be used as a method of immunologically detecting a protein, as long as it is a commonly used known method. Examples of such a method may include Western blot, enzyme linked immunosorbent assay (the ELISA method), chemiluminescence immunoassay, fluorescence immunoassay, radioimmunoassay, latex agglutination assay, immunonephelometry, and immunochromatography. Of these, Western blot and the ELISA method are preferably used.

When the detection method of the present invention is carried out by immunoassay using a labeled antibody, such as the enzyme linked immunosorbent assay (the ELISA method), chemiluminescence immunoassay, fluorescence immunoassay, or radioimmunoassay, it can also be carried out by a sandwich method or competitive method. When the sandwich method is applied, either an immobilized antibody or labeled antibody may be an anti-Cochlin antibody.

Any solid phase carrier can be used for the sandwich method, as long as it is an insoluble carrier that can be used to support an antibody. Examples of such a carrier may include: (1) those having an internal volume, such as a plate, test tube, or tube, which consists of a substance insoluble in water, including, as typical examples, a plastic consisting of a polystyrene resin, polycarbonate resin, silicon resin, nylon resin, etc., and a glass; beads; balls; filters; or membranes, and (2) insoluble carriers used for affinity chromatography, such as a cellulose carrier, agarose carrier, polyacrylamide carrier, dextran carrier, polystyrene carrier, polyvinyl alcohol carrier, polyamino acid carrier, or porous silica carrier.

Assay operations can be performed according to known methods (for example, "*Rinsho byori rinji zokan tokushu,* 53 *go, Rinsho kensa no tameno immunoassay—Gijutsu to oyo—* (Clinical Pathology, Extra edition, Vol. 53, Immunoassay for clinical tests, Techniques and applications)" edited by the Japan Society of Clinical Pathology, Clinical Pathology Publication, 1983; "*Koso meneki sokutei ho* (Enzyme immunoassay)" edited by Eiji Ishikawa et al., $3^{rd}$ edition, Igaku-Shoin Ltd., 1987; "*Tanpakushitsu kakusan koso, bessatsu No.* 31, *Koso meneki sokutei ho* (Proteins, Nucleic acids, and Enzymes, Supplementary volume No. 31, Enzyme Immunoassay)", edited by Tsunehiro Kitagawa et al., Kyoritsu Shuppan Co., Ltd., 1987).

For example, an immobilized antibody is allowed to react with a sample, and a labeled antibody is simultaneously allowed to react therewith, or a labeled antibody is allowed to react therewith after washing, so as to form a complex consisting of an immobilized antibody, an antigen, and a labeled antibody. Thereafter, unbound labeled antibodies are washed and separated, so that the amount of antigens in the sample can be determined from the amount of bound labeled antibodies. More specifically, when enzyme linked immunosorbent assay (ELISA method) is applied, a substrate is allowed to react with a labeled enzyme under optimal conditions, and the amount of reaction products is measured by an optical method or the like. When fluorescence immunoassay is applied, fluorescence intensity by fluorescence labeling is measured. When radioimmunoassay is applied, the radiation dose by radiolabeling is measured. When chemiluminescence immunoassay is applied, the amount of luminescence by a luminescence reaction system is measured.

As in the case of latex agglutination or immunonephelometry, when the detection method of the present invention is carried out by measuring the generation of an immune complex agglutinate as a transmitted light or scattered light according to an optical method, or is carried out by a measurement method involving visual observation, a phosphate buffer solution, glycine buffer solution, Tris buffer solution, or Good's buffer solution may be used as a solvent, and further, a reaction accelerator such as polyethylene glycol, or a nonspecific reaction inhibitor may also be added.

In a case where an antibody supported by a solid phase carrier is used, a particle made from a material such as polystyrene, a styrene-butadiene copolymer, a (meth)acrylic acid ester polymer, latex, gelatin, liposome, microcapsule, erythrocyte, silica, alumina, carbon black, a metallic compound, metal, ceramic, or a magnetic substance can be used as such a solid phase carrier.

Examples of a method of supporting an antibody by a solid phase carrier may include known methods such as the physical adsorption method, the chemical bond method, or a combined use thereof. Measurement can be carried out by known methods. When measurement is carried out by an optical method, for example, a sample is allowed to react with an antibody, or with an antibody supported by a solid phase carrier, and then, transmitted light or scattered light is measured by the end point assay or the rate assay.

In addition, when measurement is carried out by visual observation, a sample is allowed to react with an antibody supported by a solid phase carrier in a container such as a plate or microtiter plate, so as to visually determine the state of agglutination. Further, measurement may also be carried out using equipment such as a microplate reader instead of determining by visual observation.

By the above-described method, body fluid existing in the middle ear of a patient is analyzed as a sample. When the existence of Cochlin is detected in the sample, it can be judged that the patient is likely to have a perilymph fistula. Also, the body fluid is assayed by a known ordinary protein assay method, so as to determine the amount of Cochlin existing in the body fluid.

2. Antibody for Detection of Cochlin and Reagent Containing the Same

Any antibody can be used for the above-described immunological method, as long as it recognizes the above-described Cochlin. This is to say, the present invention provides a reagent for detection of a perilymph fistula, which comprises an anti-Cochlin antibody.

An anti-Cochlin antibody can be produced by using, as an antigen, for example, a polypeptide having the amino acid sequence shown in SEQ ID NO: 1 in the sequence listing or a partial sequence thereof (hereinafter referred to as an "antigen polypeptide" at times). More specifically, an antibody which recognizes an antigenic determinant (hereinafter referred to as an "epitope" at times) contained in an antigen polypeptide having an amino acid sequence specific for a protein consisting of the above-described N-terminal fragment (hereinafter referred to as an "anti-Cochlin N-terminal fragment antibody" at times), or the like is preferably used. Further, among such anti-Cochlin N-terminal fragment antibodies, an antibody which recognizes an antigenic determinant contained in an antigen polypeptide specific for a protein consisting of an N-terminal fragment having a molecular weight of approximately 16 kDa is particularly preferably used. More specifically, such an antibody is an antibody which recognizes an antigenic determinant contained in an amino acid sequence portion corresponding to amino acids at positions 36 to 127 of the amino acid sequence shown in SEQ ID NO: 1 in the sequence listing.

Such an antibody of the present invention is preferably an antibody that does not react with other proteins contained in body fluids other than the perilymph, which can exist in the middle ear of a human. However, any other antibodies can be used, as long as they have a sufficiently high reactivity with Cochlin and can distinguish the perilymph from other body fluids. More specifically, when detection is carried out by Western blot, for example, an antibody capable of clearly distinguishing the band derived from Cochlin from the bands derived from other proteins may be used.

As an antigen polypeptide, a sequence that has high antigenicity and is adequate as an antigenic determinant may be selected by known methods and may be used. For example, using commercially available software for analyzing epitopes, such as "Epitope Adviser" (manufactured by Fujitsu Kyushu System Engineering, Ltd.), the amino acid sequence of Cochlin is analyzed. According to such analysis, the fact that it is sterically exposed, hydrophobicity and hydrophilicity, flexibility of the structure, polarity, and other factors are comprehensively predicted, so as to select a sequence, which presumably has a shape that is likely to become an epitope. Moreover, when an antibody reacting in many types of animals is produced, for example, the amino acid sequences of Cochlin found in several types of animals of interest are aligned using suitable software for analyzing sequence data, and thus, a partial sequence that is likely to become an epitope may be selected from an amino acid sequence common in the animals. Furthermore, when an antibody specifically binding to Cochlin found in a specific animal is produced, a sequence portion having low homology with the amino acid sequences of Cochlin found in other types of animals may be selected.

The length of an antigen polypeptide is not particularly limited. An antigen polypeptide may have any length, as long as it can be recognized as an antigen in an animal immunized, when immunization is carried out using the polypeptide by a method described later. More specifically, an antigen polypeptide consisting of 5 to 30 amino acid residues, and preferably of 10 to 25 amino acid residues, can be used, for example. Such an antigen polypeptide may be either a synthetic polypeptide chemically synthesized by known methods, or polypeptide extracted and purified from natural products.

An antigen polypeptide having an amino acid sequence of Cochlin existing in the perilymph can arbitrarily be selected from polypeptides having the amino acid sequence shown in SEQ ID NO: 1 in the sequence listing or a partial sequence thereof, and can be used as an antigen polypeptide herein. As an antigen polypeptide for producing an anti-Cochlin N-terminal antibody, for example, any polypeptide can be used, as long as it has an amino acid sequence containing at least one antigenic determinant of the above-described N-terminal fragment. Specifically, from among amino acid sequence portions corresponding to amino acids at positions 36 to 127 of the amino acid sequence shown in SEQ ID NO: 1 in the sequence listing, a polypeptide having an amino acid sequence portion containing at least one antigenic determinant is preferably used. More specifically, polypeptides having amino acid sequence portions at positions 36 to 50 (SEQ ID NO: 2), 63 to 83 (SEQ ID NO: 5), 95 to 111 (SEQ ID NO: 6), and 114 to 127 (SEQ ID NO: 7) in SEQ ID NO:1 of the sequence listing, are preferably used. Of these, polypeptides having amino acid sequence portions at positions 36 to 50 (SEQ ID NO: 2) or 114 to 127 (SEQ ID NO: 7) are particularly preferable.

In addition, as an antigen polypeptide for producing an antibody capable of recognizing all three isoforms p63, p44, and p40, for example, a polypeptide having an amino acid sequence portion corresponding to amino acids at positions 163 to 181 (SEQ ID NO: 4) of the amino acid sequence shown in SEQ ID NO: 1 of the sequence listing and the like is preferably used. As an antigen polypeptide for producing an antibody capable of recognizing two isoforms p63 and p44, for example, a polypeptide having an amino acid sequence portion corresponding to amino acids at positions 137 to 151 (SEQ ID NO: 3) of the amino acid sequence shown in SEQ ID NO: 1 of the sequence listing and the like is preferably used.

The positional relationship of these antigen polypeptides on the amino acid sequence shown in SEQ ID NO: 1 is shown in FIG. 10.

An antibody can be produced by commonly used known methods. The antibody of the present invention may be either a polyclonal antibody or monoclonal antibody. A polyclonal antibody is preferably used. More specifically, when a polyclonal antibody is produced, for example, the above-described antigen polypeptide is bound to a carrier protein such as KLH (keyhole limpet hemocyanin), BSA (bovine serum albumin), or pig thyroid gland globulin, using a suitable condensing agent such as carbodiimide or maleimide, so as to produce an antigen (immunogen) used for immunization. Herein, binding of an antigen polypeptide to a carrier protein may be carried out by commonly used known methods. In the case of a method of binding an antigen polypeptide to KLH as a carrier protein using maleimide, for example, a difunctional condensing agent such as Sulfo-SMCC (Sulfosuccimidyl4-(N-maleimidomethyl)cyclohexane-1-carboxylate) is preferably allowed to react with KLH for maleimidation. Thereafter, the thus maleimidated product is allowed to react with an antigen polypeptide wherein cysteine is attached to an N-terminus or C-terminus thereof, which is to be bound. Thus, the antigen polypeptide can easily be bound to the carrier protein via thiol, so as to produce an immunogen. When cysteine is contained in the amino acid sequence of the selected antigen polypeptide, the antigen polypeptide can also be bound to the carrier protein using this cysteine. In addition, in the case of using carbodiimidated KLH, a peptide bond is formed by a dehydration-condensation reaction with an antigen polypeptide, so that the antigen polypeptide can be bound to the carrier protein.

A solution containing the thus prepared immunogen is mixed with an adjuvant as necessary, and the obtained mixture is subcutaneously or intraperitoneally injected into an animal commonly used in the production of an antibody, such as a rabbit, mouse, rat, Guinea pig, sheep, goat, or chicken, repeatedly every 2 or 3 weeks for immunization. After completion of the immunization, the blood is experimentally collected as appropriate, and it is preferably confirmed by the ELISA method, Western blot, or the like that a titer (antibody titer) has been sufficiently increased. Thereafter, the blood is collected from an animal, the titer of which is confirmed to be sufficiently increased, and the serum is separated, so as to obtain an antiserum. In the case of a chicken, a water-soluble fraction is separated from the egg yolk collected from a hen egg, and an egg yolk extract is then prepared from the fraction. This extract can also be used, as with the above antiserum.

In the present invention, the obtained antiserum or the like can be directly used without purification, but it is preferably purified before use by the following methods. Examples of a method applied herein may include: methods for purifying an immunoglobulin fraction such as a purification method of using Protein A, a salting-out method of using ammonium sulfate, or ion exchange chromatography; and a method for purifying an immunoglobulin fraction by affinity column chromatography using a column on which a specific polypeptide is immobilized. Of these, the purification method of using Protein A and the method of using affinity column chromatography are preferably used singly or in combination. Herein, as a polypeptide immobilized on a column for purification, a polypeptide having the same sequence as the amino acid sequence of an antigen polypeptide used or a partial sequence thereof may be selected and used.

In addition, when a monoclonal antibody is produced, antibody-generating cells are collected from the spleen of an animal that is immunized in the same manner as described above, and the cells are then fused with the cultured cells of myeloma cells derived from a syngeneic animal, so as to produce hybridomas (Milstein et al., Nature, 256, 495(1975)). The hybridomas are cultured, and an antibody titer is confirmed as appropriate by the ELISA method, Western blot, or the like. Thus, hybridomas, which generate monoclonal antibodies recognizing an epitope of interest and have a high ability to produce antibodies, may be selected. From the culture supernatant of the thus selected hybridomas, a monoclonal antibody of interest can be obtained.

The thus obtained antibodies all specifically recognize Cochlin. This fact can be confirmed by collecting tissues in which Cochlin has been known to exist, such as inner ear tissues, from an appropriate animal, preparing an extract from the tissues, and using the extract as a positive control. Alternatively, the fact can also be confirmed by chemically synthesizing a polypeptide having the amino acid sequence used as an antigen polypeptide, and analyzing reactivity therewith. Moreover, it is also preferable to use the perilymph as a sample and to confirm the reactivity with Cochlin existing in the perilymph.

Further, the term "antibody" is used in the present specification to mean not only a full-length antibody, but also a fragment of an antibody. Such an antibody fragment is preferably a functional fragment such as $F(ab')_2$ or Fab'. Such $F(ab')_2$ and Fab' are produced by treating immunoglobulin with protease (e.g., pepsin or papain). They are antibody fragments, which are generated by digesting before and after a disulfide bond existing between two H chains in a hinge region. Moreover, such antibody fragments include a protein comprising an antigen-binding site derived from a gene encoding the antibody.

For example, when IgG1 is treated with papain, it is cleaved upstream of the disulfide bond existing between two H chains in a hinge region, so as to produce two homologous antibody fragments, wherein an L chain fragment consisting of VL (L chain variable region) and CL (L chain constant region) and an H chain consisting of VH (H chain variable region) and CHγ1 (a γ11 region in H chain constant region) are bound to each other via a disulfide bond at the C-terminal region. Each of these two homologous antibody fragments is designated as Fab'. Also, when IgG is treated with pepsin, it is cleaved downstream of the disulfide bond existing between two H chains in a hinge region, so as to produce an antibody fragment that is slightly greater than the above antibody fragment, wherein two Fab' fragments are bound in the hinge region. This fragment is designated as $F(ab')_2$.

In addition, the antibody of the present invention can be used as an immobilized antibody that is supported on an insoluble carrier such as a solid phase carrier, or can also be used as a labeled antibody that is labeled with a labeling substance. Such an immobilized antibody and a labeled antibody are also included in the scope of the present invention.

An immobilized antibody means an antibody that is supported by an insoluble carrier by physical adsorption, chemical bond, or the like. Such an immobilized antibody can be used to detect or assay Cochlin contained in a body fluid existing in the middle ear. Examples of an insoluble carrier that can be used to support an antibody may include: (1) those having an internal volume, such as a plate, test tube, or tube, which consists of a substance insoluble in water, including, as typical examples, a plastic consisting of a polystyrene resin, polycarbonate resin, silicon resin, nylon resin, etc., and a glass; beads; balls; filters; or membranes, and (2) insoluble carriers used for affinity chromatography, such as a cellulose carrier, agarose carrier, polyacrylamide carrier, dextran carrier, polystyrene carrier, polyvinyl alcohol carrier, polyamino acid carrier, or porous silica carrier.

A labeled antibody means an antibody that is labeled with a labeling substance. Such a labeled antibody can be used to detect or assay Cochlin contained in a body fluid existing in the middle ear. A labeling substance that can be used in the present invention is not particularly limited, as long as it binds to an antibody via physical bond, chemical bond or the like, to detect the existence thereof. Specific examples of a labeling substance may include an enzyme, a fluorescent substance, a chemiluminescent substance, biotin, avidin, and a radioisotope. More specific examples may include: enzymes such as peroxidase, alkaline phosphatase, β-D-galactosidase, glucose oxidase, glucose-6-phosphate dehydrogenase, alcohol dehydrogenase, malate dehydrogenase, penicillinase, catalase, apoglucose oxidase, urease, luciferase, or acetylcholine esterase; fluorescent substances such as fluorescein isothiocyanate, phycobiliprotein, rare earth metal chelate, dansyl chloride, or tetramethylrhodamine isothiocyanate; radioisotopes such as $^3H$, $^{14}C$, $^{125}I$, or $^{131}I$; biotin; avidin; and chemiluminescent substances. As a method of binding a labeling substance to an antibody, known methods, such as a glutaraldehyde method, maleimide method, pyridyl disulfide method, or periodic acid method, can be used.

Herein, a radioisotope and a fluorescent substance can generate a detectable signal by themselves. However, since an enzyme, a chemiluminescent substance, biotin, and avidin cannot generate a detectable signal by themselves, they further react with one or more types of other substances, so as to generate a detectable signal. In the case of an enzyme, for example, at least a substrate is required, and thus, various substrates are used depending on a method of measuring enzyme activity (e.g., colorimetric method, fluorescence method, bioluminescence method, chemiluminescence method, etc.) In addition, in the case of biotin, it is common to allow the biotin to react with at least avidin or enzyme modified avidin. Various coloring substances are further used depending on the substrate, as necessary.

The above-described anti-Cochlin antibody (including a fragment thereof, a labeled antibody, an immobilized antibody, etc.) can also be used as a reagent for detection of perilymph fistulas. The form of the reagent is not particularly limited. Either a solid or liquid (a solution, a suspension, etc.) may be used. In the case of a liquid, the above antibody is dissolved or suspended in an appropriate solvent (a buffer solution capable of stably conserving an antibody), so as to prepare a reagent.

3. A Reagent Kit Used to Detect Perilymph Fistulas

The reagent kit of the present invention comprises at least an antibody for detecting the existence of Cochlin derived from the perilymph in a sample, and is used to detect the above-described perilymph fistulas. Using the reagent kit, the detection of perilymph fistulas of the present invention can be simply and quickly carried out as needed, and the results can be utilized for differentiation of the disease from other diseases, determination of treatment policy, and others.

The reagent kit of the present invention can adopt any constitution, as long as it is a constitution whereby the detection method of the present invention can be carried out. In the case of a reagent kit for detecting Cochlin by the ELISA method, for example, it comprises at least an antibody for detecting the existence of Cochlin and a secondary antibody that is enzyme-labeled, and it may further comprise a solid phase for adsorbing Cochlin existing in a sample, an enzyme substrate, a buffer solution such as a diluent or washing solution, a positive control, etc. Thus, the reagent kit of the present invention comprises at least an antibody for detecting the existence of Cochlin in a sample, and commonly used known reagents or the like are added thereto, so as to produce the present reagent kit.

EXAMPLES

The present invention will be described in the following examples. However, these examples are not intended to limit the scope of the present invention.

It is to be noted that "SDS" represents sodium dodecyl sulfate, "PBS" represents phosphate buffered saline, "DAB" represents 3,3'-diaminobenzidine, and "HRP" represents horse radish peroxidase in the following examples.

Example 1

1. Production of Antibody

The following 3 types of antibodies were produced as polyclonal antibodies to the 3 types of isoforms of Cochlin: an antibody recognizing only the isoform p63 (hereinafter referred to as an "anti-LCCL antibody" at times), an antibody recognizing the isoforms p63 and p44 (hereinafter referred to as an "anti-p63/44 antibody" at times), and an antibody recognizing all the isoforms (hereinafter referred to as an "anti-p63/44/40 antibody" at times). The production of these antibodies was ordered to an outside manufacturer, Takara Shuzo Co., Ltd.

(1) Selection of Amino Acid Sequences of Antigen Polypeptides

The amino acid sequences of Cochlins from a human, a bovine, and a mouse (N. G. Robertson, Nature Genet., 20, 299-303 (1998); Ikezono et al., Biochem. Biophys. Acta, 1535, 3, 258-265 (2001)) were subjected to alignment. A sequence that is common in these animals and has excellent antigenicity was selected, and used as an antigen polypeptide that is used to produce the 3 types of antibodies. The selection of the sequence was carried out with reference to the results obtained by analysis using "Epitope Adviser" (manufactured by Fujitsu Kyushu System Engineering, Ltd.) From the obtained results, a polypeptide (SEQ ID NO: 2) consisting of 15 amino acids, which exists at the N-terminus of the isoform p63, was selected as an antigen polypeptide used to produce an anti-LCCL antibody. This antigen polypeptide corresponds to amino acids at positions 36 to 50 of the amino acid sequence shown in SEQ ID NO: 1 in the sequence listing. A polypeptide (SEQ ID NO: 3; corresponding to amino acids at positions 137 to 151 of the amino acid sequence shown in SEQ ID NO: 1 in the sequence listing), which exists at the N-terminus of the isoform p44 and consists of 15 amino acids that are common in the isoforms p63 and p44, was selected as an antigen polypeptide used to produce an anti-p63/44 antibody. Further, a polypeptide (SEQ ID NO: 4; corresponding to amino acids at positions 163 to 181 of the amino acid sequence shown in SEQ ID NO: 1 in the sequence listing), which exists at the N-terminus of the isoform p40 and consists of 19 amino acids that are common in all the isoforms, was selected as an antigen polypeptide used to produce an anti-p63/44/40 antibody.

(2) Production of Antibodies

The production of polyclonal antibodies using the antigen polypeptides having the amino acid sequences selected in (1) above was ordered to an outside manufacturer, Takara Shuzo Co., Ltd. The procedure of the production of antibodies performed by Takara Shuzo Co., Ltd. was as follows.

First, 10 mg (80%) each of the above antigen polypeptides was prepared by chemical synthesis, and the obtained antigen polypeptide was bound to 2 mg of KLH (keyhole limpet hemocyanin) via Cys (cysteine) according to the maleimide method, so as to prepare an immunogen. With regard to antigen polypeptides used to produce an anti-p63/44 antibody and an anti-63/44/40 antibody, no cysteine is contained in their amino acid sequences. Accordingly, a polypeptide wherein cysteine was added to the C-terminus of the anti-p63/44 antibody, and a polypeptide wherein cysteine was added to the N-terminus of the anti-p63/44/40 antibody were synthesized, and the thus synthesized polypeptides were used. A rabbit was sensitized with such an immunogen 4 times in total at intervals of 2 weeks. After the third sensitization, a titer was measured by the ELISA method (the enzyme linked immunosorbent assay), and an increase in the titer was confirmed. After completion of the sensitization, 1 ml of an antiserum was collected according to known methods, and the total amount of the obtained antiserum was purified with Protein A. Thereafter, approximately 80% of the antiserum purified with Protein A was passed through a peptide affinity column, which had been prepared in advance by binding 5 mg of the above antigen polypeptide to 5 g of sepharose activated with CNBr, so that it could be further purified. Each of these operations was carried out in accordance with commonly used known methods.

(3) Confirmation of Specificity of Antibodies

Specificity of the antibodies produced in (2) above was confirmed by Western blot by using, as an antigen, an inner ear protein solution (positive control) prepared from bovine inner ear tissues.

First, 1 ml of a protein extract solution (obtained by dissolving 1 tab of Complete mini Ca(−) (manufactured by Boehringer Mannheim) in 10 ml of PBS and 0.5% SDS (pH 7.4)) was added to 180 mg of the inner ear membranous labyrinth collected from bovine temporal bone (purchased from Tokyo Shibaura Zoki) in ice. The mixture was then homogenized with a Labtube Mixer and a Disposable Stirring Pestle (manufactured by GHI) until residual tissues could not be observed by the naked eye. Thereafter, the homogenate was subjected to centrifugation at 1,000 g for 15 minutes, and the obtained supernatant was defined as an inner ear protein solution. As a positive control, 0.5 µl of the solution was used. Western blot was carried out by the method that will be described in detail in 2 later.

As a result, a band was observed at a position of approximately 63 kDa in analysis using an anti-LCCL antibody, and thus, it was confirmed that this antibody recognizes the isoform p63. In analysis using an anti-p63/44 antibody, bands were detected at positions of approximately 63 kDa and 44 kDa, and thus, it was confirmed that this antibody recognizes the isoforms p63 and p44. Further, in analysis using an anti-p63/44/40 antibody, three bands of isoforms p63, p44, and p40 were detected, and thus, it was confirmed that this antibody recognizes all the isoforms. Thus, it was found that 3 types of isoforms of Cochlin existing in inner ear tissues was distinguished from one another, using the produced 3 types of antibodies.

2. Analysis of Perilymph and Inner Ear Tissues Using Antibodies Produced in 1 Above Using the 3 types of antibodies produced in 1 above, the perilymph and the inner ear tissues were analyzed by Western blot.

(1) Preparation of Reagent Used in Electrophoresis and Western Blot (i) Preparation of Sample Buffer Distilled water was added to 18.75 ml of 1 M Tris-HCl (pH 6.8), 15 ml of 2-mercaptoethanol, 30 ml of glycerol, 6.9 ml of 10% SDS, and 3 ml of 0.1% bromophenol blue, so as to prepare 100 ml of a solution in total. As the final concentrations, 0.188 M Tris buffer and 2.39 mM SDS were obtained.

(ii) Preparation of Size Marker 1 vial of a commercially available size marker (prestained protein marker weight standards, high range prestained protein molecular weight standard (used for high molecular weight); Cat.No. #26041-020 (manufactured by Gibco) was dissolved in 500 µl of 1 mM DTT and 10% glycerol, followed by boiling for 5 minutes. Thereafter, the solution was cooled and then poured into tubes dividedly at 20 µl/tube, followed by conservation at −80° C. When used, it was melted.

(iii) Preparation of Running Buffer 15 g/l Tris Base, 72 g/l Glycine, and 5 g/l SDS were dissolved in MilliQ water (manufactured by MILLIPORE), so as to prepare a 5× concentrate as a stock solution. When used, this concentrate was diluted, and a diluted solution containing 25 mM Tris, 192 mM glycine, and 1 g/l SDS (pH 8.3) as the final concentrations was used.

(iv) Preparation of Transfer Buffer 3.03 g of Tris, 14.4 g of glycine, and 200 ml of methanol were dissolved in distilled water to the final concentrations of 25 mM Tris, 192 mM glycine, and 20% v/v methanol (pH 8.3).

(v) 0.1% Tween PBS (pH 7.4) Was Used as a Washing Buffer.

(vi) Preparation of Blocking Buffer

Dry milk (skimmed milk manufactured by Snow Brand Milk Products Co., Ltd.) was dissolved in 0.2% Tween in PBS (pH 7.4) to the final concentration of 5%.

(vii) Preparation of Antibody Dilution Buffer

Dry milk (skimmed milk manufactured by Snow Brand Milk Products Co., Ltd.) was dissolved in 0.1% Tween in PBS (pH 7.4) to the final concentration of 1%.

(viii) Preparation of Ponceau S Staining Solution 30 g of trichloroacetic acid, 30 g of sulfosalicyclic acid, and 2 g of Ponceau S were dissolved in 100 ml of MilliQ water, so as to prepare a 10× concentrate as a stock solution. When used, the concentrate was 10 times diluted with MilliQ water.

(ix) Preparation of DAB Solution

A DAB solution was prepared when it was used. 10 mg of DAB (10 mg tablet; Cat.No. 049-22831 (manufactured by Wako)) was dissolved in 20 ml of 50 mM Tris buffer (pH 7.6), and 20 µl of 30% $H_2O_2$ was then added thereto. The obtained mixture was filtrated with a 0.45 µm filter (manufactured by MILLIPORE) and then used.

(2) Preparation of Sample

The inner ear tissues and the perilymph obtained from a human, a bovine, and a Guinea pig were used as samples.

In order to collect a human sample, a sufficient explanation was given to the patient regarding the purpose of collecting a sample and the use of the sample for research purposes, and thus, patients gave full informed consent for the use of the specimens. With regard to an inner ear tissue extract solution, human inner ear membranous labyrinth collected during acoustic neuroma surgery was measured, and 1 ml of a protein extract solution (obtained by dissolving 1 tab of Complete mini Ca(−) (manufactured by Boehringer Mannheim) in 10 ml of PBS and 0.5% SDS (pH 7.4)) was added to 180 mg of the tissues. The mixture was then homogenized with a Labtube Mixer and a Disposable Stirring Pestle (manufactured by GHI) until residual tissues could not be observed by the naked eye. Thereafter, the homogenate was subjected to centrifugation at 1,000 g for 15 minutes, and the obtained supernatant was defined as an inner ear protein solution. 2 μl and 0.5 μl of the inner ear protein solutions were used in electrophoresis. With regard to the perilymph, a pore was made with a drill on the basal turn perilymphatic space of the cochlea during the operation to insert a cochlear implant, and the perilymph leaked when an electrode was inserted was recovered. 2 μl of the obtained perilymph was used in electrophoresis.

With regard to a bovine sample, 0.5 μl of the product prepared in 1(3) above was used in the same manner as in 1 above. In addition, the external auditory meatus of a bovine temporal bone (purchased from Tokyo Shibaura Zoki) was drilled with a surgical drill. The tympanic membrane was excised, and after the drill reached the middle ear, the stapes was excised, so that the perilymph could be collected from the oval window. During this operation, an attention was paid such that the perilymph was collected without mixing the inner ear tissues therein. 2 μl of the collected perilymph was used as a sample. With regard to a Guinea pig inner ear tissue extract solution, 1 ml of a protein solution (obtained by dissolving 1 tab of Complete mini Ca(−) (manufactured by Boehringer Mannheim) in 10 ml of PBS and 0.5% SDS (pH 7.4)) was added to 180 mg of the inner ear membranous labyrinth collected from a Hartley Guinea pig temporal bone (purchased from Sankyo Labo Service) in ice. The mixture was then homogenized with a Labtube Mixer and a Disposable Stirring Pestle (manufactured by GHI) until residual tissues could not be observed by the naked eye. Thereafter, the homogenate was subjected to centrifugation at 1,000 g for 15 minutes, and the obtained supernatant was defined as an inner ear protein solution. 0.5 μl of the inner ear protein solution was used. With regard to the perilymph, the tympanic membrane was excised, and after the drill reached the middle ear, the stapes was excised, so that the perilymph could be collected from the oval window. 2 μl of the perilymph was used.

With respect to 200 parts by volume of each sample, 85 parts by volume of the sample buffer prepared in (1) above and 15 parts by volume of 2-mercaptoethanol were mixed and dissolved. Each of the thus prepared sample solutions was incubated at 95° C. for 3 minutes. Thereafter, the solution was then cooled to room temperature, and it was then subjected to centrifugation at 3,000 rpm for 10 seconds. 15 μl each of the centrifugate was subjected to electrophoresis.

(3) Polyacrylamide Gel Electrophoresis

In order to detect each antibody, each of the sample solutions prepared in (2) above was applied to each of the total 3 slices of 15% polyacrylamide gels (ReadyGel J; 73 mm long× 80 mm wide×1 mm thick (manufactured by Bio-Rad), and it was then mounted on an electrophoresis apparatus (manufactured by Bio-Rad), followed by performing electrophoresis by using the running buffer prepared in (1) above. The electrophoresis was carried out for 60 minutes at 27 mA [per slice of the gel].

(4) Analysis by Western Blot

Each of the 3 slices of gels which were subjected to electrophoresis in (3) above was transferred to a nitrocellulose membrane (0.45 μm; Cat.no.#162-0145 (manufactured by Bio-Rad)) at 100 V for 90 minutes using the transfer buffer prepared in (1) above. A wet blotter (manufactured by Bio-Rad) was used as a transfer apparatus.

After completion of the transfer, the nitrocellulose membrane was immersed in a Ponceau staining solution for 5 minutes. Thereafter, washing was carried out in MilliQ water, and it was confirmed that a protein became stained in each sample solution. After confirmation, washing was carried out in distilled water for 5 minutes under vibration.

Subsequently, detection and analysis were carried out by DAB staining method (enzyme coloration method). First, each of the above 3 slices of nitrocellulose membranes was immersed in a blocking buffer at 4° C. over day and night to block a non-specific reaction. Thereafter, it was washed with a washing buffer for 5 minutes 3 times, and it was then allowed to react with the primary antibody prepared in 1 above. To prepare the primary antibody, in the case of an anti-LCCL antibody, it was 1,000 times diluted with an antibody dilution buffer, and in the case of an anti-p63/44 antibody and an anti-p63/44/40 antibody, they were 500 times diluted with the same above buffer. Thereafter, each of the thus prepared antibodies was added to a nitrocellulose membrane. The reaction was carried out for 2 hours under vibration.

The membrane obtained as a result of the reaction was washed with the above washing buffer for 15 minutes 3 times, and it was then allowed to react with a secondary antibody. A goat-derived anti-rabbit IgG antibody (labeled with HRP; Cat.No.p-0448 (manufactured by Dako)) that had been 1,000 times diluted with the above antibody dilution buffer was used as a secondary antibody. The secondary antibody was reacted for 1 hour under vibration. The reaction product was washed with the above washing buffer for 15 minutes 3 times, and it was then allowed to react with the DAB solution prepared in (1) above for coloration. The reaction was terminated by immersing the reaction product in distilled water.

The results of each analysis are shown in FIG. 1.

As a result of the analysis using an anti-LCCL antibody, a band of 63 kDa (a band indicated with an arrow in the figure) was detected in the inner ear tissue extract solution collected from all the animals, a human, a bovine, and a Guinea pig. With regard to the perilymph, a clear thin band of 16 kDa (a band indicated with an asterisk (*) in the figure) was detected in the perilymph collected from all the animals. As a result of the analysis using an anti-p63/44 antibody, bands of 63 kDa and 44 kDa were detected in the inner ear tissue extract solution collected from all the animals, but no significant band was observed in the perilymph collected therefrom. As a result of the analysis using an anti-p63/44/40 antibody, 3 bands of 63 kDa, 44 kDa, and 40 kDa were detected in the inner ear extract solution collected from all the animals, but no significant band was observed in the perilymph collected therefrom.

From these results, it was confirmed that these 3 types of antibodies showed the same reaction in all types of animals, and thus that 3 types of isoforms could be distinguished. In addition, it was found that a protein of approximately 16 kDa exists in the perilymph. This protein was recognized only by the anti-LCCL antibody but was not recognized by the anti-p63/44 antibody and the anti-p63/44/40 antibody. Thus, it was suggested that this protein consists of a fragment having the amino acid sequence at the N-terminus of the isoform p63 (a sequence which neither p44 nor p40 has).

Focusing attention on this protein of 16 kDa existing only in the perilymph, further studies have been made using the anti-LCCL antibody.

3. Detection of Perilymph Fistulas Using Anti-LCCL Antibody

As a result of the analysis described in 2 above, a protein of 16 kDa existing only in the perilymph was detected by the antibody of the present invention. Next, a method for detecting perilymph fistulas using the above protein as an indicator has been studied. The anti-LCCL antibody was used in the studies.

(1) Preparation of Reagent for Electrophoresis and Western Blot

Reagents were all prepared in the same manner as in 2(1) above.

(2) Preparation of Sample

CSF, serum, saliva, a middle ear lavage containing an exudate generated due to otitis media with effusion, and a middle ear lavage containing otorrhoea generated due to chronic otitis media were used as body fluids other than the perilymph, which can exist in the middle ear of a human. For an attempt to detect perilymph fistulas, a middle ear lavage collected from a patient likely to have a perilymph fistula, who developed acute sensorineural deafness, was used. As a disease to be distinguished from the perilymph fistula, a middle ear lavage obtained from a patient with Meniere's disease was used. Moreover, the perilymphs leaked from inner ears of patients who underwent a cochlear implant surgery, stapes surgery, fistula of lateral semicircular canal caused by total resection of external ear canal for the treatment of cancer of the external ear canal, and head trauma, were used as samples. Regarding each sample, a sufficient explanation was given to the patient regarding the purpose of collecting a sample and the use of the sample for research purposes, and thus, patients gave full informed consent for the use of the specimens.

Regarding CSF, a portion of CSF collected from a patient, who underwent an examination for suspected meningitis and cerebritis, and as a result, was judged to be normal, was used. The venous blood of a healthy subject was used as a serum. A saliva collected from a healthy subject was used. With regard to a middle ear lavage containing an exudate generated due to otitis media with effusion, a middle ear lavage containing otorrhoea generated due to chronic otitis media, and a middle ear lavage collected from a patient with Meniere's disease, the tympanic membrane of each patient was slightly excised, and a small amount of saline solution was injected therein using a syringe. Thereafter, the solution was recovered using a syringe again. The middle ear lavage of a patient likely to have a perilymph fistula was collected, when exploratory tympanotomy was carried out. In the case of collecting a middle ear lavage before the surgery for a perilymph fistula, exploratory tympanotomy was not carried out, but the middle ear lavage was recovered from the tympanic membrane using a syringe, as in the case of collecting a middle ear lavage from a patient with Meniere's disease.

The perilymph leaked from the inner ear of patients with various diseases was collected as follows. With regard to the perilymph of a patient who underwent the operation to insert a cochlear implant, a pore was made with a drill on the basal turn perilymphatic space of the cochlea during the operation, and the perilymph leaked when an electrode was inserted was recovered. With regard to the perilymph of a patient who underwent stapes surgery for otosclerosis, a pore was made on the foot plate (oval window) of the stapes, and the perilymph leaked when ossicular prosthesis was inserted was recovered. Moreover, with regard to a middle ear lavage before subjecting to stapes surgery, the middle ear was washed with a saline solution before stapedotomy, and the middle ear lavage was recovered. With regard to the perilymph of a patient with lateral semicircular canal fistula, when total extirpation of the external acoustic meatus was carried out to excise carcinoma of the external auditory canal, a pore made on the prominence of the lateral semicircular canal and a peripheral portion thereof were washed with a saline solution, and the middle ear lavage was recovered. With regard to the perilymph of a patient who experienced head trauma, the perilymph leaked due to inner ear fracture caused by head trauma (a bloody middle ear exudate due to traumatic temporal bone fracture) was collected. Moreover, the perilymph collected from a patient who underwent the operation to insert a cochlear implant was 5 times, 50 times, and 500 times diluted, so as to prepare diluents. These diluents were also used.

These samples, and the bovine perilymph and bovine inner ear protein solution (positive control) used in Example 2 above were divided as shown in Table 1 indicated below. 85 parts by volume of the sample buffer prepared in (1) above and 15 parts by volume of 2-mercaptoethanol were mixed into 200 parts by volume of the above each sample, and were then dissolved therein. Each of the thus prepared sample solutions was incubated at 95° C. for 3 minutes. Thereafter, it was cooled to room temperature and was then subjected to centrifugation at 3,000 rpm for 10 seconds. 15 µl each of an aliquot was separated from the centrifugate, and it was then subjected to electrophoresis.

(3) Polyacrylamide Gel Electrophoresis

Each of the sample solutions prepared in (2) above was applied to 15% polyacrylamide gels (ReadyGel J; 73 mm long×80 mm wide×1 mm thick (manufactured by Bio-Rad)), and it was then mounted on an electrophoresis apparatus (manufactured by Bio-Rad), followed by performing electrophoresis, using the running buffer prepared in (1) above. The electrophoresis was carried out for 60 minutes at 27 mA [per slice of the gel].

(4) Analysis by Western Blot

The gel which was subjected to electrophoresis in (3) above was transferred into a nitrocellulose membrane (0.45 µm; Cat.no.#162-0145 (manufactured by Bio-Rad)) at 100 V for 90 minutes using the transfer buffer prepared in (1) above. A wet blotter (manufactured by Bio-Rad) was used as a blotting apparatus.

After completion of the blotting, the nitrocellulose membrane was immersed in a Ponceau staining solution for 5 minutes. Thereafter, washing was carried out in MilliQ water, and it was confirmed that a protein became stained in each sample solution was observed. After confirmation, washing was carried out in distilled water for 5 minutes under vibration.

Subsequently, detection and analysis were carried out by the chemiluminescence method. After completion of the blotting, the nitrocellulose membrane was immersed in a blocking buffer at 4° C. over day and night to block a non-specific reaction. Thereafter, it was washed with a washing buffer for 5 minutes 3 times, and it was then allowed to react with a primary antibody. The LCCL antibody that had been 1,000 times diluted with an antibody dilution buffer was used as a primary antibody, and the primary antibody was added to the nitrocellulose membrane. The reaction was carried out for 2 hours under vibration.

A goat-derived anti-rabbit IgG antibody (labeled with HRP) (Cat.No.p-0448; manufactured by Dako) that had been 1,000 times diluted with the above antibody dilution buffer was used as a secondary antibody. The reaction was carried out for 1 hour under vibration. The reaction product was washed with the above washing buffer for 15 minutes 3 times, and it was then subjected to chemiluminescence using a chemiluminescence kit (ECL plus; manufactured by Amersham Pharmacia Biotech). The generated signal was exposed to a film (Kodak Scientific Imaging Film; Cat. No. #165-1454 (manufactured by Kodak)). In the case of a first nitrocellulose membrane onto which samples with well Nos. 1 to 12 in Table 1 were blotted, the exposure time of the film was set at approximately 1 minute. In the case of a second nitrocellulose membrane onto which samples with well Nos. 13 to 24 were blotted, it was set at 1 hour. In the case of a third nitrocellulose membrane onto which samples with well Nos. 25 to 36 were blotted, 2 types of experiments were carried out. That is, in one experiment, the exposure time was set at 10 seconds, and in the other experiment, it was set at 1 hour. Thus, a comparison was made regarding a difference caused by the exposure time. In the cases of a fourth nitrocellulose membrane onto which samples with well Nos. 37 to 48 were blotted, a fifth nitrocellulose membrane onto which samples with well Nos. 49 to 60 were blotted, and a sixth nitrocellulose membrane onto which samples with well Nos. 61 to 72 were blotted, the exposure time was set at 5 minutes.

Figure 2:
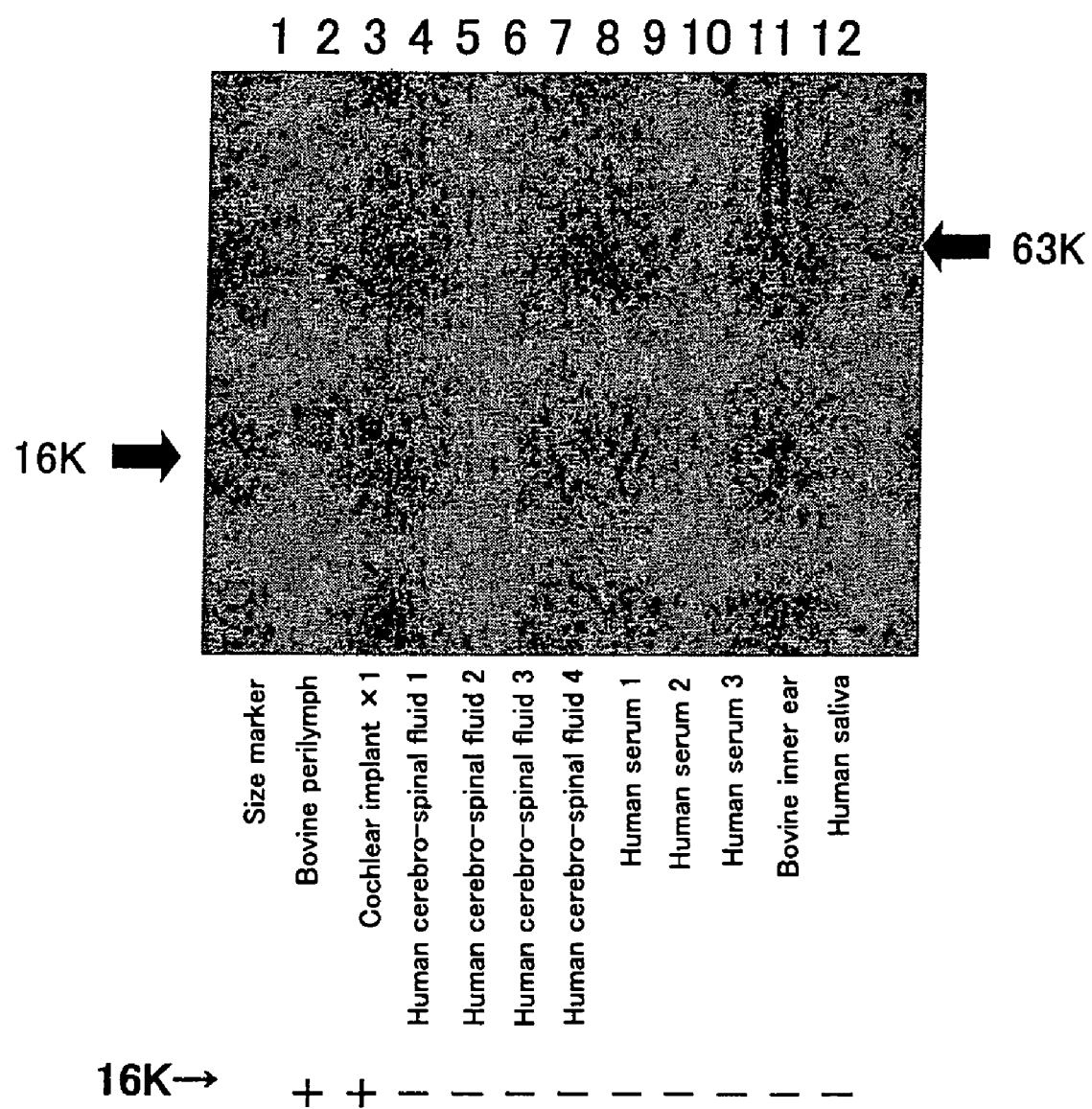
FIG. 2 shows the results obtained by analyzing various types of samples derived from humans by Western blot, using the anti-LCCL antibody. In the figure, well numbers from 1 to 12 correspond to well numbers used in Table 1, and the description below each photograph indicates a sample subjected to the well. With regard to the description below the name of each sample, "+" represents the fact that a protein with 16 kDa was detected, and "−" represents the fact that such a protein was not detected.
Figure 3:
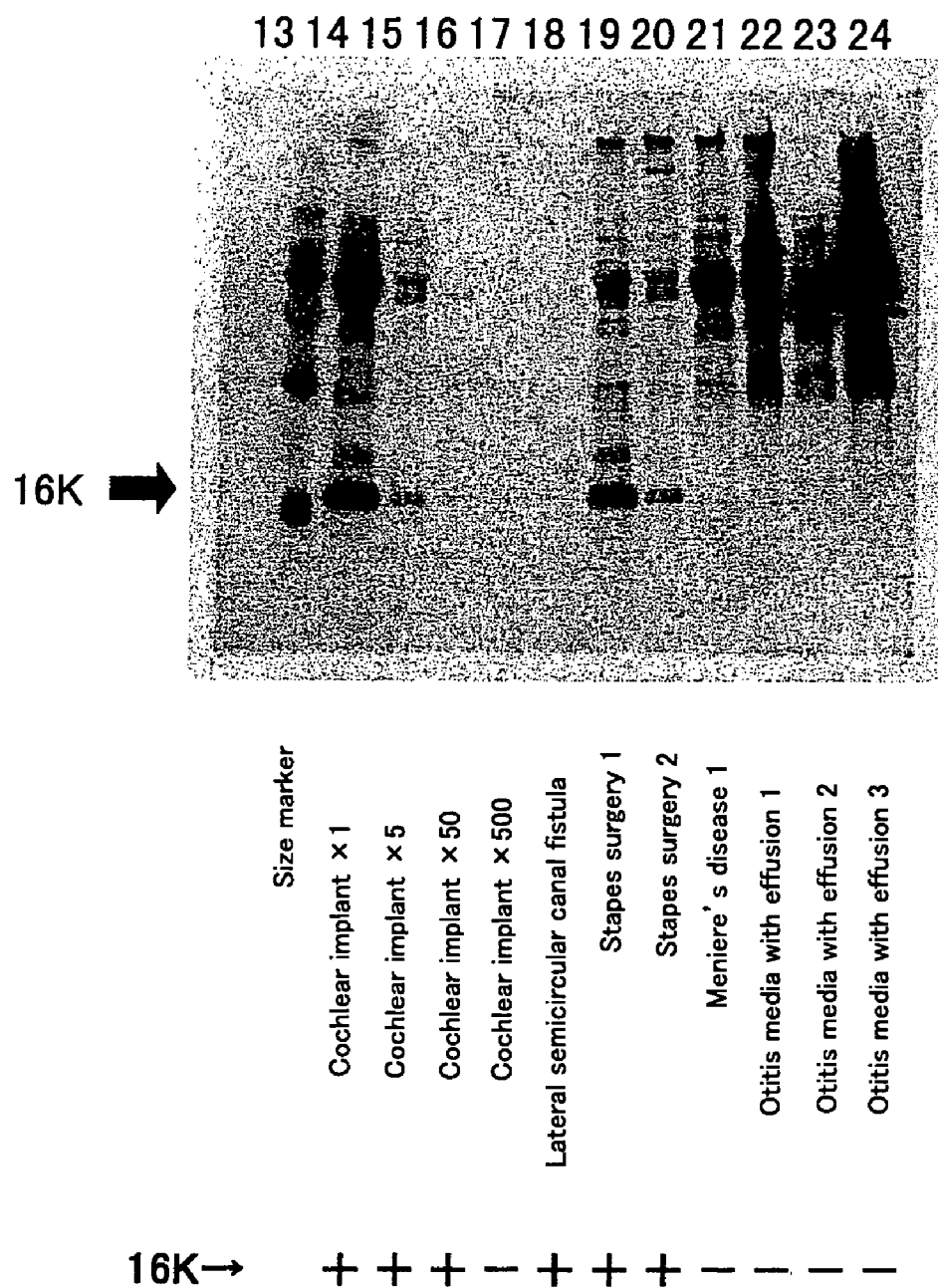
FIG. 3 shows the results obtained by analyzing various types of samples derived from humans by Western blot, using the anti-LCCL antibody. In the figure, well numbers from 13 to 24 correspond to well numbers used in Table 1, and the description below each photograph indicates a sample subjected to the well. With regard to the description below the name of each sample, "+" represents a protein with 16 kDa was detected, and "−" represents the fact that such a protein was not detected.
Figure 4:
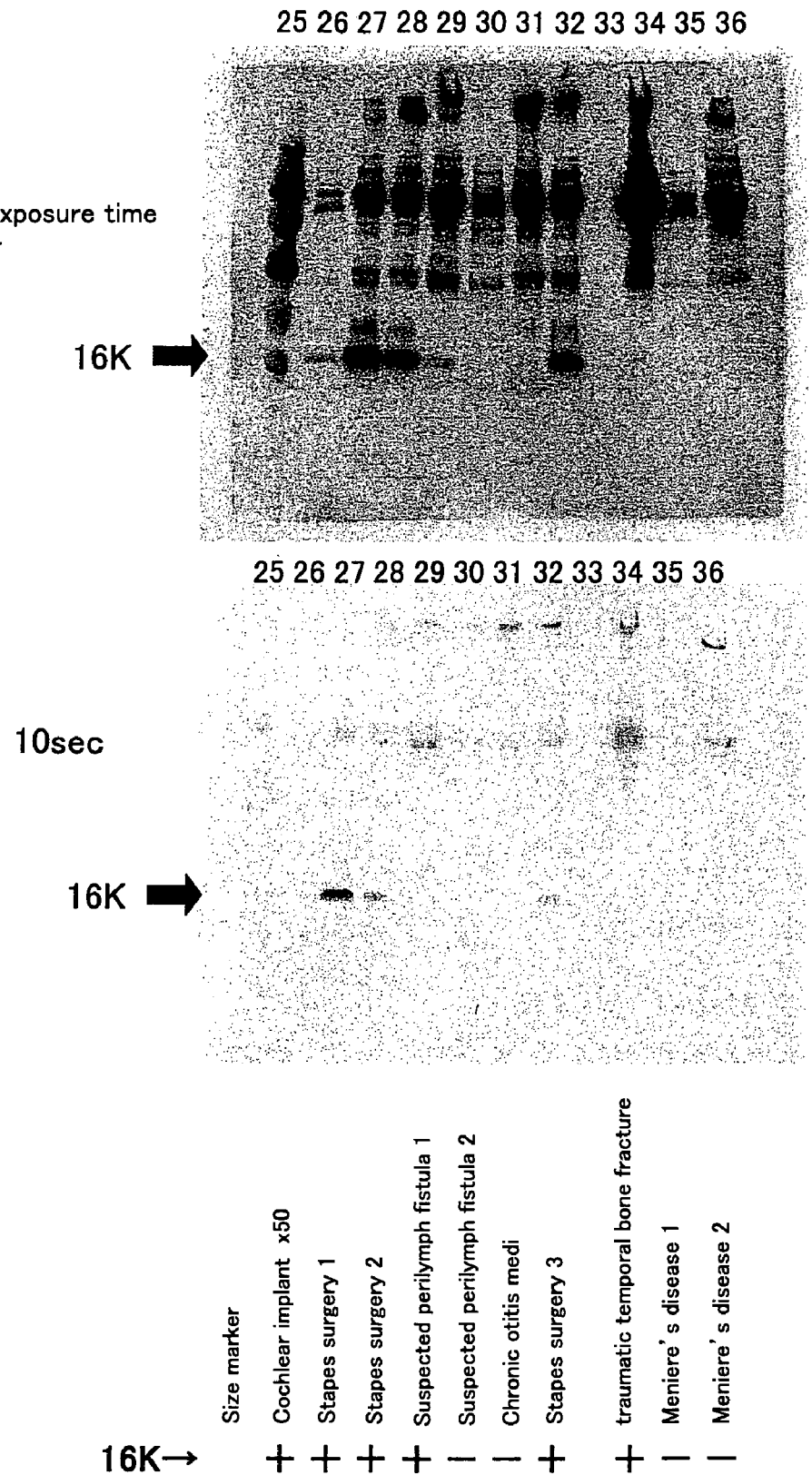
FIG. 4 shows the results obtained by analyzing various types of samples derived from humans by Western blot, using the anti-LCCL antibody. In the figure, well numbers from 25 to 36 correspond to well numbers used in Table 1, and the description below each photograph indicates a sample subjected to the well. With regard to the description below the name of each sample, "+" represents the fact that a protein with 16 kDa was detected, and "−" represents the fact that such a protein was not detected. The upper photograph shows the results obtained when a nitrocellulose membrane was exposed to a film for 1 hour during the chemiluminescence method. The lower photograph shows the results obtained when the same nitrocellulose membrane was exposed to a film for 10 seconds.
Figure 5:
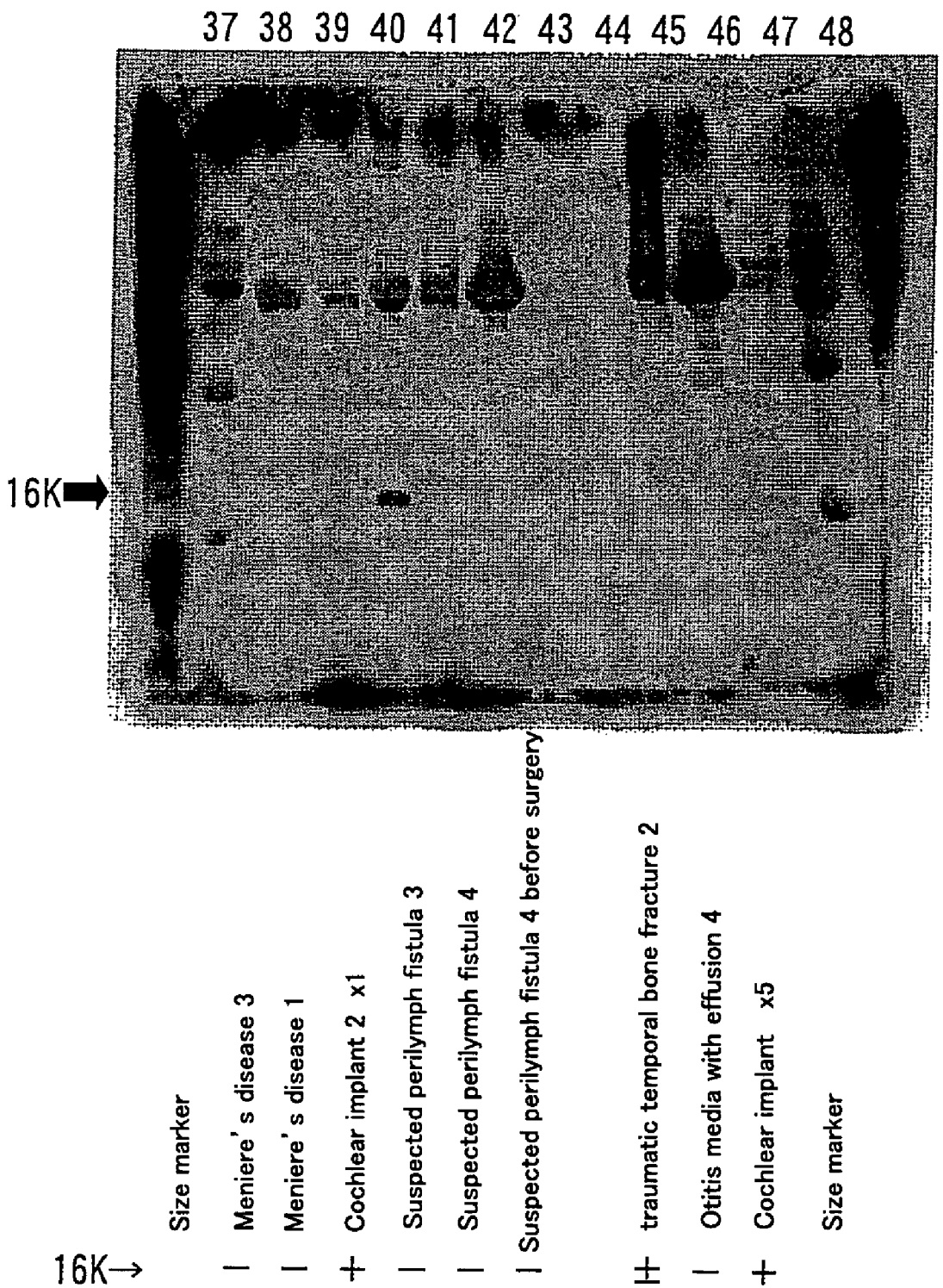
FIG. 5 shows the results obtained by analyzing various types of samples derived from humans by Western blot, using the anti-LCCL antibody. In the figure, well numbers from 37 to 48 correspond to well numbers used in Table 1, and the description below each photograph indicates a sample subjected to the well. With regard to the description below the name of each sample, "+" represents the fact that a protein with 16 kDa was detected, and "−" represents the fact that such a protein was not detected. In addition, "±" represents the fact that the result could not be determined.
Figure 6:
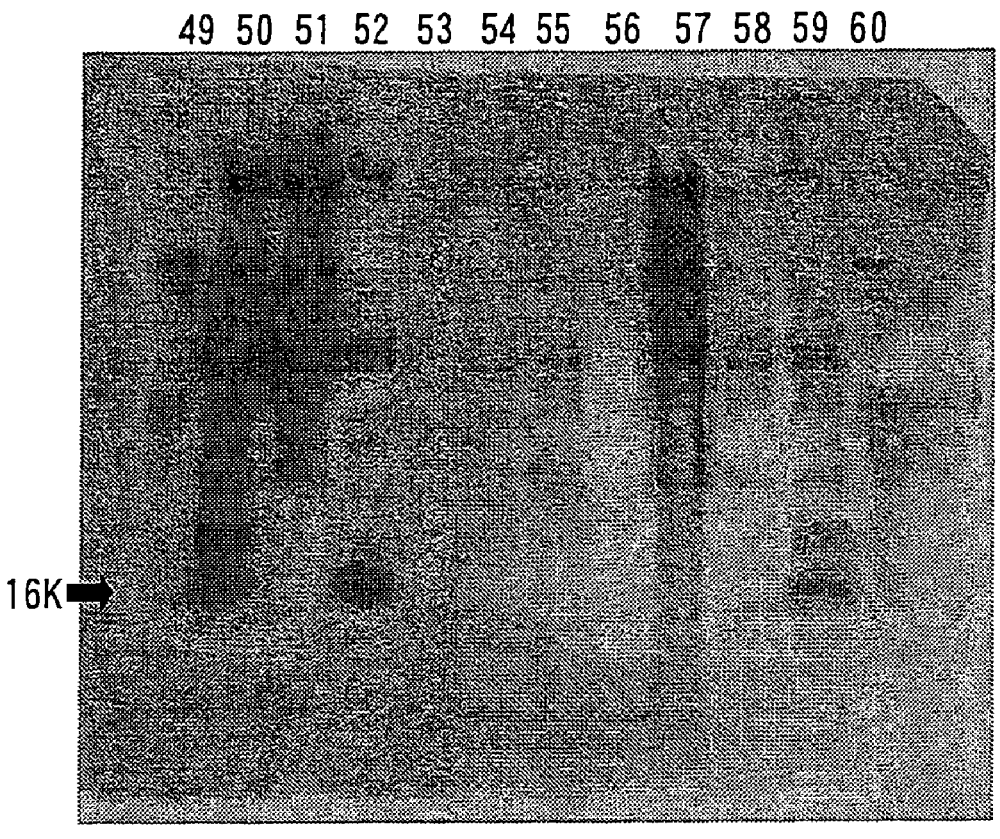
FIG. 6 shows the results obtained by analyzing various types of samples derived from humans by Western blot, using the anti-LCCL antibody. In the figure, well numbers from 49 to 60 correspond to well numbers used in Table 1, and the description below each photograph indicates a sample subjected to the well. With regard to the description below the name of each sample, "+" represents the fact that a protein with 16 kDa was detected, and "−" represents the fact that such a protein was not detected.
Figure 6:
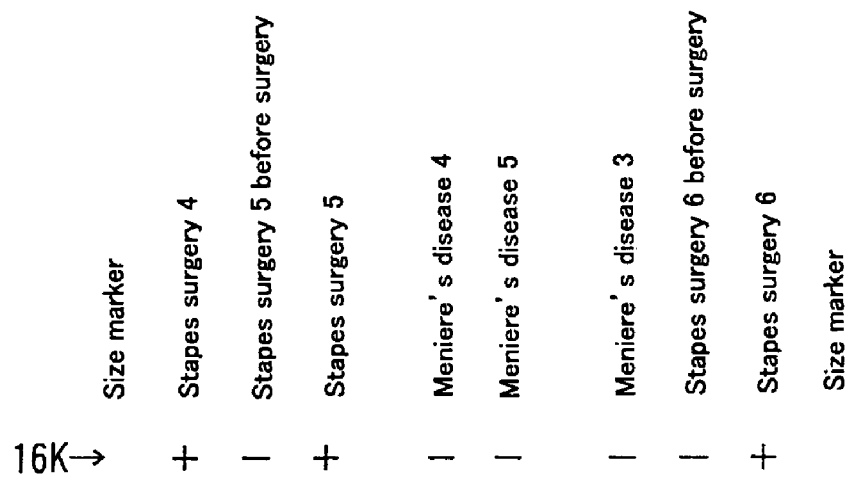
Figure 7:
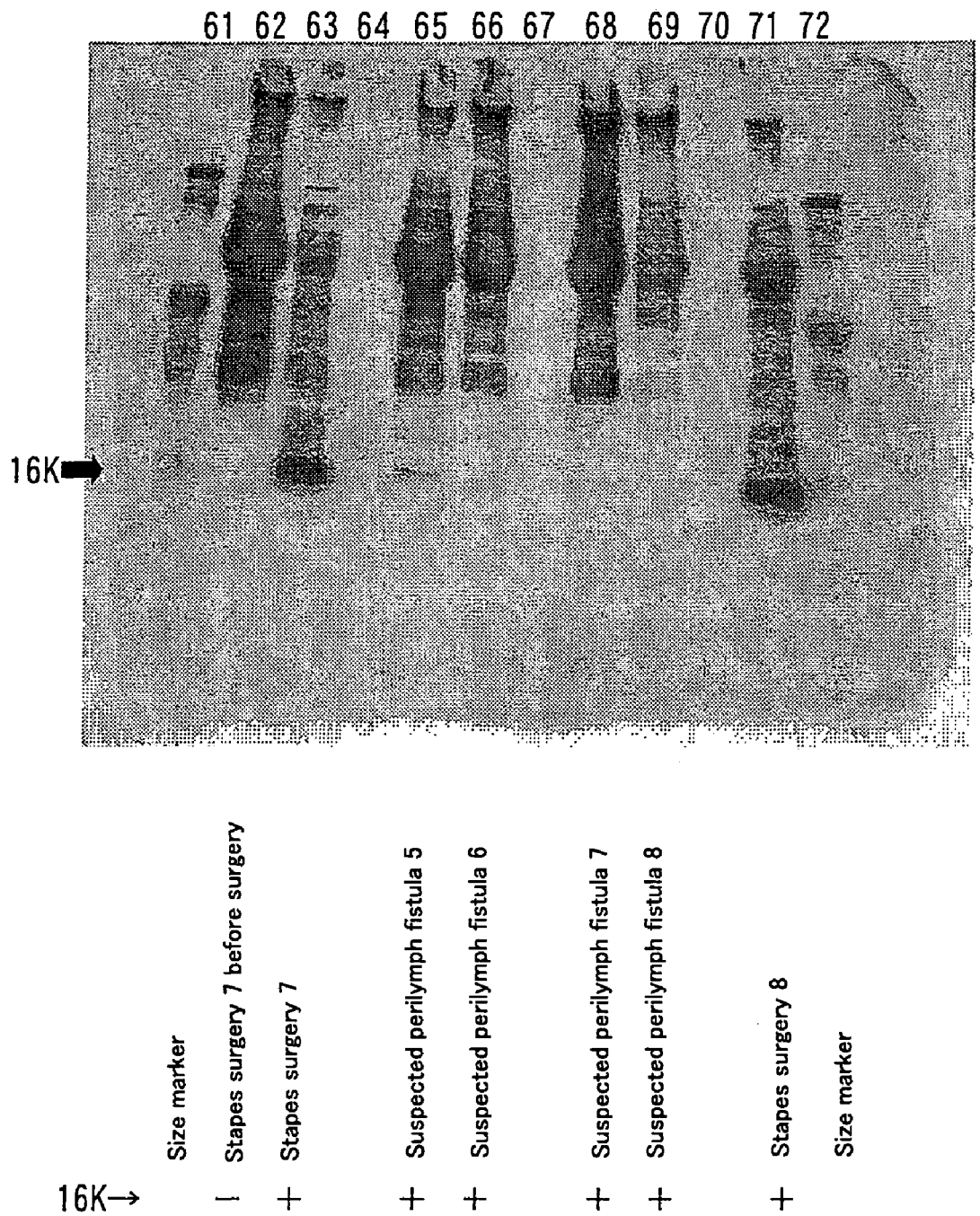
FIG. 7 shows the results obtained by analyzing various types of samples derived from humans by Western blot, using the anti-LCCL antibody. In the figure, well numbers from 61 to 72 correspond to well numbers used in Table 1, and the description below each photograph indicates a sample subjected to the well. With regard to the description below the name of each sample, "+" represents the fact that a protein with 16 kDa was detected, and "−" represents the fact that such a protein was not detected.

The results are shown in FIGS. 2 to 7. In the figures, the number indicated above the photograph represents the well number shown in Table 1, and the description indicated below the photograph represents a sample placed on the well. FIG. 2 is a photograph showing the results of detection by the chemiluminescence method of a first nitrocellulose membrane onto which samples with well Nos. 1 to 12 shown in Table 1 were blotted. FIG. 3 is a photograph showing the results regarding a second nitrocellulose membrane onto which samples with well Nos. 13 to 24 were blotted. FIG. 4 is a photograph showing the results regarding a third nitrocellulose membrane onto which samples with well Nos. 25 to 36 were blotted. FIG. 5 is a photograph showing the results regarding a fourth nitrocellulose membrane onto which samples with well Nos. 37 to 48 were blotted. FIG. 6 is a photograph showing the results regarding a fifth nitrocellulose membrane onto which samples with well Nos. 49 to 60 were blotted. FIG. 7 is a photograph showing the results regarding a sixth nitrocellulose membrane onto which samples with well Nos. 61 to 72 were blotted. The amount of each sample subjected to electrophoresis, well number, and the obtained results are shown in Table 1.

TABLE 1

| Sample name | | Well No. | Amount of sample separated (μl) | Results |
| --- | --- | --- | --- | --- |
| Human cerebro-spinal fluid (CSF) 1-4 | | 4-7 | 7 | − |
| Human serum 1-3 | | 8-10 | 3/100 | − |
| Human saliva | | 12 | 7 | − |
| Cochlear implant | 1 × 1 | 3, 14 | 2 | + |
| | 2 × 1 | 40 | 2 | + |
| | 1 × 5 | 15, 47 | 2 | + |
| | 1 × 50 | 16, 26 | 2 | + |
| | 1 × 500 | 17 | 2 | − |
| Lateral semicircular canal fistula | | 18 | 2 | + |

TABLE 1-continued

| Sample name | | Well No. | Amount of sample separated (μl) | Results |
| --- | --- | --- | --- | --- |
| Stapes surgery | 1 | 19, 27 | 2 | + |
| | 2 | 20, 28 | 4 | + |
| | 3 | 32 | 0.5 | + |
| | 4 | 50 | 2 | + |
| | 5 | 52 | 2 | + |
| | 6 | 59 | 2 | + |
| | 7 | 63 | 2 | + |
| | 8 | 71 | 2 | + |
| Before undergoing stapes surgery | 5 | 51 | 16 | − |
| | 6 | 58 | 16 | − |
| | 7 | 62 | 16 | − |
| Meniere's disease | 1 | 21, 35, 39 | 10 | − |
| | 2 | 36 | 10 | − |
| | 3 | 38, 57 | 16 | − |
| | 4 | 54 | 16 | − |
| | 5 | 55 | 16 | − |
| Otitis media with effusion | 1 | 22 | 2 | − |
| | 2 | 23 | 2 | − |
| | 3 | 24 | 2 | − |
| | 4 | 46 | 0.5 | − |
| Chronic otitis media | | 31 | 10 | − |
| Bloody middle ear exudate due to traumatic temporal bone fracture | 1 | 34 | 2 | + |
| | 2 | 45 | 2 | ± |
| Suspected perilymph fistula | 1 | 29 | 10 | + |
| | 2 | 30 | 16 | − |
| | 3 | 41 | 16 | − |
| | 4 | 42 | 16 | − |
| | 5 | 65 | 16 | + |
| | 6 | 66 | 16 | + |
| | 7 | 68 | 16 | + |
| | 8 | 69 | 16 | + |
| Before undergoing the operation for suspected perilymph fistula | 4 | 43 | 16 | − |
| *Bovine* perilymph | | 2 | 2 | + |
| *Bovine* inner ear tissue extract solution | | 11 | 0.5 | − (+ in the case of 63k) |
| Size marker | | 1, 13, 25, 37, 48, 49, 60, 61, 72 | | |

In the case of well Nos. 33, 44, 53, 56, 64, 67, and 70, no samples were applied.

In the case of human perilymph (which was obtained from each of patients who underwent the operation to insert a cochlear implant (3 in FIG. 2, 14 to 17 in FIG. 3, 26 in FIG. 4, and 40 and 47 in FIG. 5), a patient with lateral semicircular canal fistula (18 in FIG. 3), patients who underwent stapes surgery (19 and 20 in FIG. 3, 27, 28 and 32 in FIG. 4, 50, 52 and 59 in FIG. 6, and 63 and 71 in FIG. 7), and a patient who experienced head trauma (34 in FIG. 4)), a clear thin band was detected at approximately 16 kDa in all the cases. From the results of wells wherein the perilymph derived from patients who underwent the operation to insert a cochlear implant was subjected to serial dilution (14 to 17 in FIG. 3), it was found that the perilymph collected from a human is detectable although it is approximately 50 times diluted. With regard to the middle ear lavages obtained from patients likely to have a perilymph fistula, 5 cases were determined to be positive, and 3 cases were determined to be negative (that is, 29 in FIG. 4, and 65, 66, 68 and 69 in FIG. 7 were determined to be positive; and 30 in FIG. 4, and 41 and 42 in FIG. 5 were determined to be negative. In the case of the middle ear lavage obtained from each of patients before stapes surgery (51 and 58 in FIG. 6, and 62 in FIG. 7), patients with Meniere's disease (21 in FIG. 3, 35 and 36 in FIG. 4, 38 and 39 in FIG. 5, and 54, 55 and 57 in FIG. 6), patients with otitis media with effusion (22 to 24 in FIG. 3), and a patient with chronic otitis media (31 in FIG. 4), the obtained middle ear lavarge was determined to be negative. In the case of human CSF (4 to 7 in FIG. 2), human serum (8 to 10 in FIG. 2), and human saliva (12 in FIG. 2) also, no bands were detected with the above antibodies.

In the case of bovine perilymph, a somewhat broad band of 16 kDa was detected (2 in FIG. 2). A band of 63 kDa, which was considered to be the isoform p63, was detected in a bovine inner ear protein solution as a positive control. However, since the amount of the protein was too large, it resulted in over exposure, and the corresponding portion appeared as if it had been blanked (11 in FIG. 2).

In addition, as shown in FIG. 4, when exposure was carried out for 1 hour (the upper photograph in FIG. 4), bands other than the N-terminal fragment of approximately 16 kDa were also detected, but these bands could be clearly distinguished from a band of interest. For example, especially in the case of the perilymph from a patient with head trauma (34 in FIG. 4) and the like, a band, which was considered to be albumin, was detected at approximately 60 kDa due to hemolysis generated during the collection of the perilymph. However, it could be clearly distinguished from a band of interest detected at 16 kDa. Moreover, it was also confirmed that Cochlin existing in a sample could be detected by exposure for 10 seconds (the lower photograph in FIG. 4).

From these results, it was found that the protein of 16 kDa is not detected at all in other body fluids likely to exist in the middle ear of a human, that is, CSF, serum, saliva, a middle ear lavarge before stapes surgery, a middle ear exudate generated due to otitis media with effusion, an otorrhoea generated due to chronic otitis media, and so on, and that it is also not detected in a middle ear lavarge obtained from a patient with Meniere's disease. Thus, it was found that this protein is detected only in human perilymph and is extremely useful for detection of perilymph fistulas.

Moreover, the same results were obtained in the case of using a middle ear lavarge recovered from the tympanic membrane of a patient likely to have a perilymph fistula using a syringe before undergoing surgery, and in the case of using a middle ear lavarge recovered during exploratory tympanotomy. From the results, it was found that perilymph fistulas can be detected by microincision and the use of a syringe according to the detection method of the present invention, without performing exploratory tympanotomy.

Example 2

1. Production of Antibody

As with Example 1, in addition to the anti-LCCL antibody, 3 types of antibodies recognizing only the isoform p63 were produced. The production of antibodies was ordered to an outside manufacturer, Takara Shuzo Co., Ltd.

(1) Selection of Amino Acid Sequences of Antigen Polypeptides

As antigen polypeptides used to produce 3 types of antibodies recognizing only the isoform p63, the following polypeptides were selected: a polypeptide (SEQ ID NO: 5) consisting of 21 amino acids corresponding to amino acids at positions 63 to 83 of the amino acid sequence shown in SEQ ID NO: 1 in the sequence listing (an antibody produced using this antigen polypeptide is hereinafter referred to as "anti-LCCL1 antibody" at times); a polypeptide (SEQ ID NO: 6) consisting of 17 amino acids corresponding to amino acids at positions 95 to 111 of the amino acid sequence shown in SEQ ID NO: 1 (an antibody produced using this antigen polypeptide is hereinafter referred to as "anti-LCCL2 antibody" at times); and a polypeptide (SEQ ID NO: 7) consisting of 14 amino acids corresponding to amino acids at positions 114 to 127 of the amino acid sequence shown in SEQ ID NO: 1 (an antibody produced using this antigen polypeptide is hereinafter referred to as "anti-LCCL3 antibody" at times).

(2) Production of Antibodies

The production of polyclonal antibodies using the antigen polypeptides having the amino acid sequences selected in (1) above was ordered to an outside manufacturer, Takara Shuzo Co., Ltd. The procedure of the production of antibodies was the same as described in Example 1-1(2).

With regard to the anti-LCCL2 antibody and the anti-LCCL3 antibody, no cysteine is contained in their amino acid sequences. Accordingly, a polypeptide wherein cysteine was added to the C-terminus of the antigen polypeptide used to produce each antibody was synthesized and used.

(3) Confirmation of Specificity of Antibodies

The specificity of the antibodies produced in (2) above was confirmed in the same manner as described in Example 1-1 (3). As a result, a band was observed at a position of approximately 63 kDa in the analysis of the anti-LCCL1 antibody, the anti-LCCL2 antibody, and the anti-LCCL3, and thus, it was confirmed that the antibodies recognize the isoform p63.

2. Analysis of Perilymph and Inner Ear Tissues Using Antibodies Produced in 1 Above Using the 3 types of antibodies produced in 1 above, the perilymph and the inner ear tissues were analyzed by Western blot.

(1) Preparation of Reagents for Electrophoresis and Western Blot

All operations were carried out in the same manner as described in Example 1-2(1).

(2) Preparation of Sample

The inner ear tissues and the perilymph obtained from a bovine were used as samples. An inner ear tissue extract solution was prepared by the same method as described in Example 1-1(3) above, and 0.3 µl of the solution was used. In addition, the external auditory meatus of a bovine temporal bone (purchased from Tokyo Shibaura Zoki) was drilled with a surgical drill. The tympanic membrane was excised, and after the drill reached the middle ear, the stapes was excised, so that the perilymph could be collected from the oval window. During the operation, an attention was paid such that the perilymph was collected without mixing the inner ear tissues therein. 1 µl of the collected perilymph was used as a sample.

With respect to 200 parts by volume of each sample, 85 parts by volume of the sample buffer prepared in (1) above and 15 parts by volume of 2-mercaptoethanol were mixed and dissolved. Each of the thus prepared sample solutions was incubated at 95° C. for 3 minutes. Thereafter, the solution was then cooled to room temperature, and it was then subjected to centrifugation at 3,000 rpm for 10 seconds. 15 µl each of the centrifugate was subjected to electrophoresis.

(3) Polyacrylamide Gel Electrophoresis

In order to detect each antibody, 2 slices of 15% polyacrylamide gels (ReadyGel J; 73 mm long×80 mm wide×1 mm thick (manufactured by Bio-Rad)) were prepared, wherein only the bovine inner ear sample solution prepared (2) above was applied to one slice, and only the perilymph sample solution was applied to the other. The polyacrylamide gel was then mounted on an electrophoresis apparatus (manufactured by Bio-Rad), followed by performing electrophoresis, using the running buffer prepared in (1) above. The electrophoresis was carried out for 60 minutes at 27 mA (per slice of the gel).

(4) Analysis by Western Blot

Each of the 2 slices of gels which were subjected to electrophoresis in (3) above was transferred to a nitrocellulose membrane (0.45 µm; Cat.no.#162-0145 (manufactured by Bio-Rad)) at 100 V for 90 minutes using the transfer buffer prepared in (1) above. A wet blotter (manufactured by Bio-Rad) was used as a transfer apparatus.

After completion of the transfer, the nitrocellulose membrane was immersed in a Ponceau staining solution for 5 minutes. Thereafter, washing was carried out in MilliQ water, and it was confirmed that a protein became stained in each sample solution.

Subsequently, detection and analysis were carried out by DAB staining method (enzyme coloration method). First, each of the above nitrocellulose membranes was immersed in a blocking buffer at 4° C. over day and night to block a non-specific reaction. Thereafter, it was washed with a washing buffer for 5 minutes 3 times. To prepare a primary antibody, all of the anti-LCCL antibody, the anti-LCCL1 antibody, the anti-LCCL2 antibody, and the anti-LCCL3 antibody were 1,000 times diluted with an antibody dilution buffer, and each of the thus diluted antibodies was added to a nitrocellulose membrane. The reaction was carried out for 2 hours under vibration.

The membrane obtained as a result of the reaction was washed with the above washing buffer for 15 minutes 3 times, and it was then allowed to react with a secondary antibody. A goat-derived anti-rabbit IgG antibody (labeled with HRP; Cat.No.p-0448 (manufactured by Dako)) was 1,000 times diluted with the above antibody dilution buffer, and the thus obtained antibody was used as a secondary antibody. The reaction was carried out for 1 hour under vibration. The reaction product was washed with the above washing buffer for 15 minutes 3 times, and it was then allowed to react with the DAB solution prepared in (1) above for coloration. The reaction was terminated by immersing the reaction product in distilled water.

Figure 8:
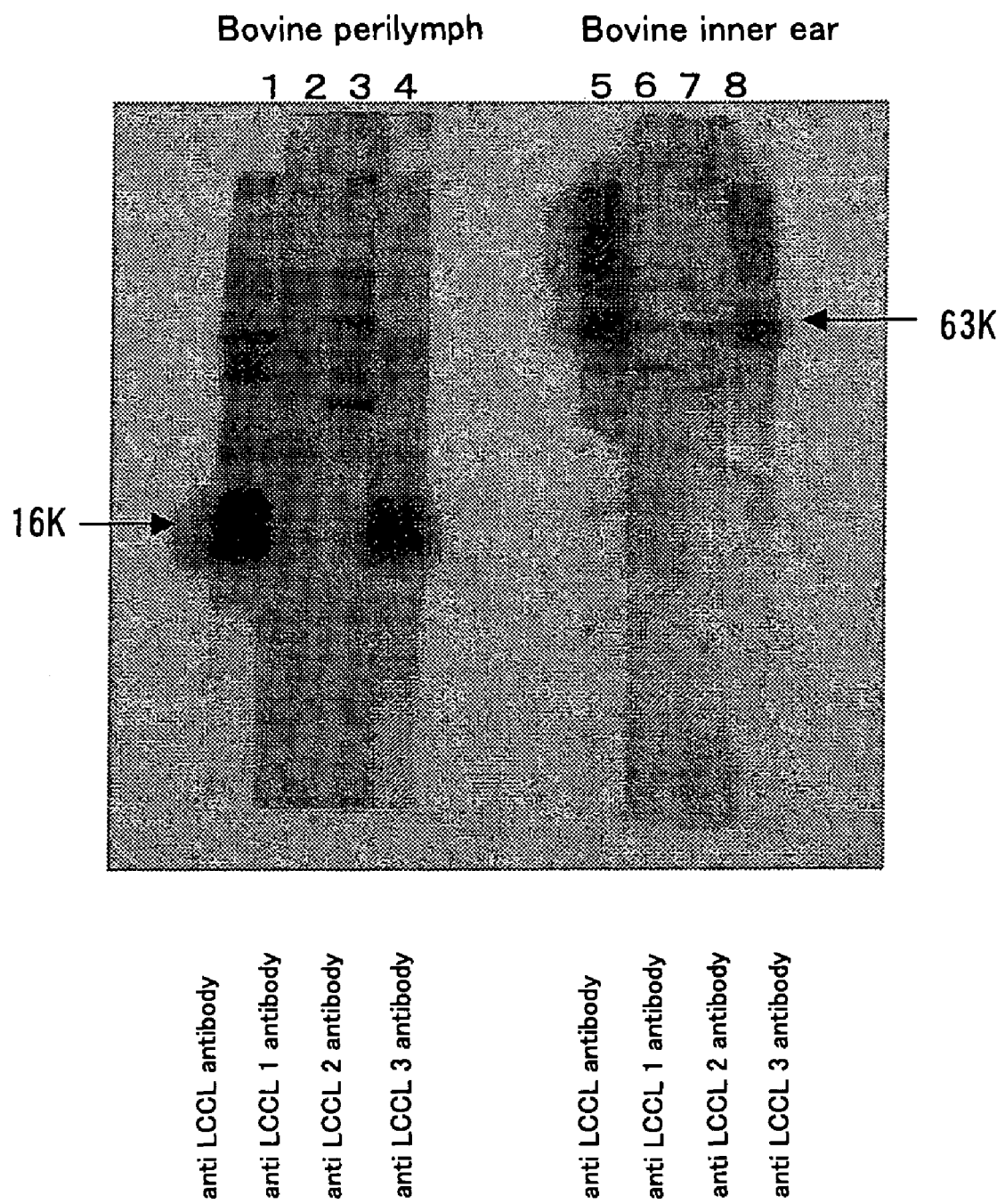
FIG. 8 shows the results obtained by analyzing bovine perilymphs and bovine inner ear tissue extracts by Western blot, using 4 types of antibodies, an anti-LCCL antibody, an anti-LCCL1 antibody, an anti-LCCL2 antibody, and an anti-LCCL3 antibody.

Lanes representing the bovine perilymph sample and the bovine inner ear sample were cut into rectangles, and arranged in the order of the antibodies, followed by analysis. The results obtained by the analysis are shown in FIG. 8.

As a result of the analysis using the anti-LCCL antibody, the anti-LCCL1 antibody, the anti-LCCL2 antibody, and the anti-LCCL3 antibody, a band of 63 kDa (a band indicated with an arrow in the figure) was detected in the inner ear tissue extract solution. With regard to the perilymph, clear bands of 16 kDa were detected regarding the anti-LCCL antibody and the anti-LCCL3 antibody. In addition, bands were detected also regarding the anti-LCCL1 antibody and the anti-LCCL2 antibody. From these results, it was confirmed that the above 4 antibodies recognize the isoform p63. Further, it was found that the protein of 16 kDa existing only in the perilymph can be recognized by the anti-LCCL antibody, the anti-LCCL1 antibody, the anti-LCCL2 antibody, and the anti-LCCL3 antibody.

3. Detection of Perilymph Fistulas Using Anti-LCCL3 Antibody

As a result of the analysis in 2 above, the protein of 16 kDa existing only in the perilymph was also detected using the anti-LCCL1 antibody, the anti-LCCL2 antibody, and the anti-LCCL3 antibody. Thus, a method for detecting perilymph fistulas using this protein as an indicator was then studied. The anti-LCCL3 antibody was used for the studies.

(1) Preparation of Reagents for Western Blot

Reagents were all prepared in the same manner as in Example 1-2(1) above.

(2) Preparation of Sample

A middle ear lavage collected from a patient with Meniere's disease, perilymph samples leaked from the inner ears of patients who underwent the operation to insert an a cochlear implant or stapes surgery, and a middle ear lavage collected from a patient likely to have a perilymph fistula, were used as samples. Regarding each sample, a sufficient explanation was given to the patient regarding the purpose of collecting a sample and the use of the sample for research purposes, and thus, patients gave full informed consent for the use of the specimens.

Samples were collected in the same manner as described in Example 1-3(2), or those collected in Example 1-3(2) were used. In order to prepare the samples, the same methods as those described in Example 1-3(2) were applied.

(3) Polyacrylamide Gel Electrophoresis

Polyacrylamide gel electrophoresis was carried out completely in the same manner as described in Example 1-3(3) above.

(4) Analysis by Western Blot

Western blot was carried out completely in the same manner as in Example 1-3(4), except that the exposure time to the film was set at 5 minutes.

Figure 9:
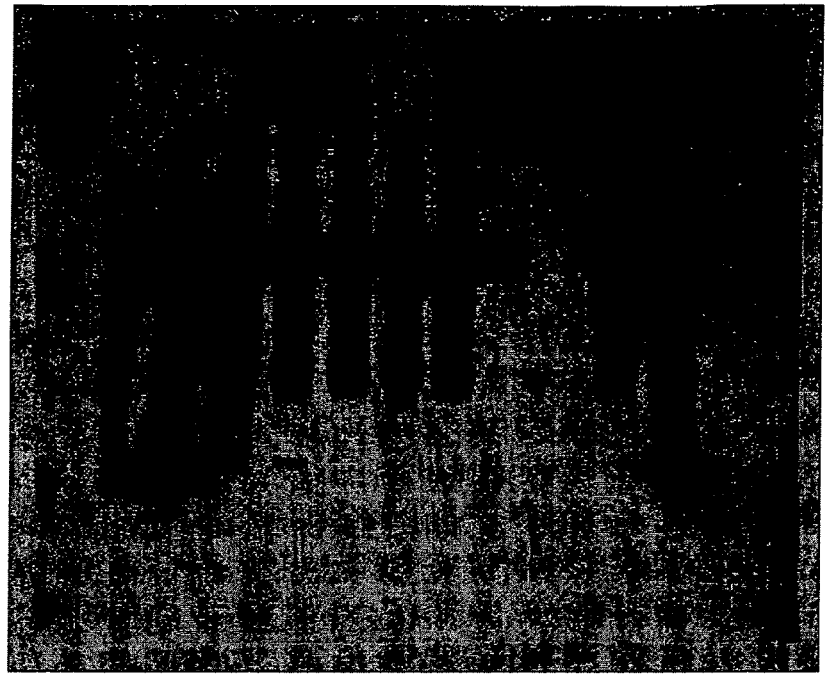
FIG. 9 shows the results obtained by analyzing various types of samples derived from humans by Western blot, using the anti-LCCL3 antibody. The lower figure is a view obtained by increasing the resolution of the portion around 16 kDa of the upper figure. In the figure, well numbers from 73 to 83 correspond to well numbers used in Table 2, and the description below each photograph indicates a sample subjected to the well. With regard to the description below the name of each sample, "+" represents the fact that a protein with 16 kDa was detected, and "−" represents the fact that such a protein was not detected.
Figure 9:
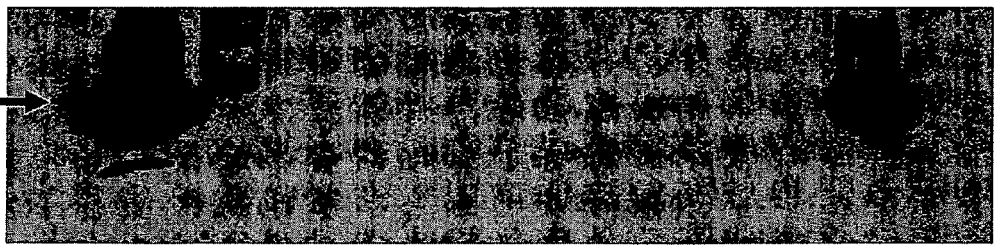

The results are shown in FIG. 9. In the figure, the number indicated above the photograph represents the well number shown in Table 2, and the description indicated below the photograph represents a sample placed on the well. FIG. 9 is a photograph showing the results of detection by the chemiluminescence method of a nitrocellulose membrane onto which samples with well Nos. 73 to 83 shown in Table 2 were blotted. The amount of each sample subjected to electrophoresis, well number, and the obtained results are shown in Table 2. With regard to samples collected from the same patients who provided samples used for the anti-LCCL antibody, test results of the samples regarding the anti-LCCL antibody are also shown for comparison.

TABLE 2

|  |  |  |  | Amount | Results | |
| --- | --- | --- | --- | --- | --- | --- |
|  |  | Well No. |  | of sample separated (µl) | Anti-LCCL antibody | Anti-LCCL3 antibody |
| Sample name |  | LCCL | LCCL3 |  |  |  |
| Cochlear implant 3 |  |  | 74 | 2 |  | + |
| Meniere's disease 3 |  | 38, 57 | 75 | 16 | − | − |
| Suspected perilymph fistula | 5 | 65 | 76 | 16 | + | + |
|  | 6 | 66 | 77 | 16 | + | + |
|  | 7 | 68 | 78 | 16 | + | + |
|  | 8 | 69 | 79 | 16 | + | + |
|  | 4 | 42 | 80 | 16 | − | − |
| Stapes surgery | 9 |  | 82 | 2 |  | + |
|  | 7 | 63 | 83 | 2 | + | + |
| Size marker |  |  | 73 |  |  |  |

* No samples were applied to well No. 81.

A band of 16 kDa was detected in human perilymph (the operation to insert a cochlear implant (74 in FIG. 9) and stapes surgery (82 and 83 in FIG. 9)), and thus, it could be confirmed that they were positive. The middle ear lavarge collected from a patient with Meniere's disease (75 in FIG. 9) was determined to be negative. With regard to the middle ear lavarge collected from a patient likely to have a perilymph fistula, 4 cases were determined to be positive and 1 case was determined to be negative (positive: 76, 77, 78 and 79 in FIG. 9; negative: 80 in FIG. 9). These results match with the results obtained regarding the anti-LCCL antibody. Since both anti-LCCL3 antibody and anti-LCCL antibody detected the protein of 16 kDa existing only in the perilymph, it was found that the anti-LCCL3 antibody is also useful for detecting perilymph fistulas, as with the anti-LCCL antibody.

Example 3

As described in detail in Examples 1 and 2 above, using the anti-LCCL antibody and the anti-LCCL3 antibody, a protein of approximately 16 kD was detected in the perilymph obtained from a human, a bovine, a Guinea pig, and others. Hence, next, analysis by two-dimensional gel electrophoresis (2D-GE) was carried out using bovine perilymph.

In the two-dimensional gel electrophoresis (2D-GE), isoelectric gel electrophoresis is carried out for the first dimension, and polyacrylamide gel electrophoresis (SDS-PAGE) is carried out for the second dimension, so that a protein can be analyzed more in detail. For example, the two-dimensional gel electrophoresis enables the separation of a plurality of proteins, which cannot be separated by the one-dimensional SDS-PAGE alone because their molecular weights are close to one another, or the analysis of a subtle change in a protein caused by various factors such as phosphorylation, addition of sugar chains, or substitution of amino acids. 2D-GE, blotting, and staining by the anti-LCCL antibody and the anti-LCCL3 antibody were carried out by methods described in detail below.

1. The First Dimensional Isoelectric Electrophoresis

Isoelectric electrophoresis for the first dimension was carried out using IPG gel (pH 6 to 9, 18 cm) manufactured by Amersham Bioscience (Buckinghamshire, U. K.). The same bovine perilymph as described in Example 1 above was used as a sample.

First, 7 parts by volume (112 μl) of an additive solution (obtained by adding 1 tablet consisting of 7 M urea, 2 M thiourea, 2% Triton X-100, 2% pharmalyte, 40 mM DTT, and a protease inhibitor (Complete mini EDTA(-), Boehringer Mannheim, Mannheim, Germany) to 100 ml) was added to 1 part by volume (approximately 16 μl) of the sample (bovine perilymph), so as to prepare a sample solution. IPG gel (purchased in a dry state) was swollen with approximately 10 ml of a swelling water (7M urea, 2M thiourea, 2% Triton X-100, 2% pharmalyte, and 40 mM DTT), and the obtained solution was used in electrophoresis for the first dimension.

Electrophoresis was carried out using an electrophoresis apparatus (Multiphor II) manufactured by Amersham Bioscience. 120 μl of the above sample solution was applied to a sample cup disposed on the anode side and then subjected to electrophoresis. Electrophoresis was carried out at 300 V for 60 seconds, and thereafter, the electric voltage was increased from 300 V to 3,500 V over 90 minutes. Thereafter, electrophoresis was further carried out at 3,500 V for 18 hours. The apparatus was cooled to 15° C. during electrophoresis.

2. The Second Dimensional SDS-PAGE Electrophoresis

After completion of the first dimensional electrophoresis, IPG gel was equilibrated with an equilibrating solution (7M urea, 25% glycerol, 50 mM Tris-HCl buffer solution (pH 6.8), 2% SDS, 33 mM DTT, and 1.6% bromophenol blue) for 30 minutes, and the resultant product was then subjected to the second dimensional SDS-polyacrylamide electrophoresis (SDS-PAGE). Gel with a size of 24×24×0.1 cm was used in SDS-PAGE. When this gel was used for concentration, the concentration of polyacrylamide was 3%. When this gel was used for separation, the concentration of polyacrylamide was 15%. Other compositions of the gel were the same as those in general SDS-PAGE. In addition, a buffer solution with the composition consisting of 25 mM Tris, 192 mM glycine, and 0.1% SDS was used in electrophoresis. Electrophoresis was carried out at 50 mA in the gel for concentration and at 70 mA in the gel for separation.

3. Blotting

Immediately after completion of the second dimensional electrophoresis, the gel was equilibrated with a buffer solution for blotting (25 mM Tris, 192 mM glycine, 0.05% SDS, and 10% methanol) for 30 minutes, and the resultant product was transferred to a PVDF membrane (manufactured by Applied Biosystems; Pro-Blot) using a blotting apparatus (Nihon Eido; NA-1515B).

4. Staining with Anti-LCCL Antibody

The membrane blotted in 3 above was placed in a blocking solution (5% skimmed milk, 0.2% Tween 20, and PBS), and it was left at rest in a refrigerator at 4° C. over day and night for blocking. Thereafter, it was stirred in a washing solution (Tween 20 and PBS) for 5 minutes 3 times for washing.

As a primary antibody solution, the anti-LCCL antibody (6 μl) produced in Example 1 above was 1,000 times diluted with a diluent (1% skimmed milk, Tween 20, and PBS; 6 ml), and the obtained solution was used. This primary antibody solution was added to a membrane that had been washed in advance, and the mixture was stirred at room temperature for 2 hours for reaction. Thereafter, the reaction product was stirred in a washing solution for 15 minutes 3 times for washing.

As a secondary antibody solution, anti-rabbit IgG-HRP conjugate (manufactured by Chappel; 2.4 μl) was 2,500 times diluted with the above diluent, and the obtained solution was used. This secondary antibody solution was added to a membrane that had been washed in advance, and the mixture was stirred at room temperature for 1 hour for reaction. Thereafter, the reaction product was stirred in a washing solution for 15 minutes 3 times for washing. An ECL kit manufactured by Amersham Bioscience was applied to the washed membrane, so as to detect spots that were recognized by antibodies.

As a result, a group of proteins were detected around an isoelectric point between 7.7 and 7.9 and a molecular weight between 17.7 and 23.1 kD. Among them, a principal protein was a protein having a molecular weight between 17.7 and 18.8 kD. It was considered that this group of proteins was not a mixture consisting of multiple proteins, but that a single protein was subtly changed by various factors such as phosphorylation, addition of sugar chains, or substitution of amino acids.

5. Staining with Anti-LCCL3 Antibody

After completion of the detection with the ECL kit described in 4 above, the used membrane was immersed in a stripping solution (100 mM 2-mercaptomethanol, 2% SDS, and 62.5 mM Tris-HCl buffer solution (pH 6.8)), and the solution was then stirred in an incubator at 50° C. for 30 minutes to strip (eliminate) the anti-LCCL antibody.

Subsequently, the same membrane was stained with the anti-LCCL3 antibody produced in Example 2 above. The procedure of staining was completely the same as in the case of staining with the anti-LCCL antibody described in 4 above. The dilution ratio of the primary antibody (anti-LCCL3 antibody) was set at 1,000 times.

As a result of the staining, proteins were detected in the same pattern as that obtained in 4 above.

As a result of the immunostaining with two types of antibodies described in 4 and 5 above, it was found that the pattern of the detected protein spots was the same. Thus, it was confirmed that the anti-LCCL antibody produced in the above Example 1 and the anti-LCCL 3 antibody produced in the above Example 2 detect the same protein. This is to say, from these results, it was found that both anti-LCCL antibody and anti-LCCL3 antibody can be equivalently used for the method for detecting of perilymph fistulas of the present invention.

Moreover, the antigen polypeptide used to produce the anti-LCCL antibody is a peptide corresponding to amino acids at positions 36 to 50 of the amino acid sequence shown in SEQ ID NO: 1 in the sequence listing, and the antigen polypeptide used to produce the anti-LCCL3 antibody is a peptide corresponding to amino acids at positions 114 to 127 thereof. Thus, it was confirmed that the protein of approximately 16 kD detected in the perilymph in Examples 1 and 2 above is a protein consisting of the N-terminal fragment of Cochlin containing almost of the amino acid sequence portion corresponding to amino acids at positions 36 to 127 shown in SEQ ID NO: 1. Accordingly, it was found that antibodies used for the method for detecting of perilymph fistulas of the present invention are not limited to the anti-LCCL antibody, anti-LCCL1 antibody, anti-LCCL2 antibody, and anti-LCCL3 antibody, which were produced in the present examples, but also that antibodies recognizing antigenic determinants contained in the amino acid sequence portion corresponding to amino acids at positions 36 to 127 of the amino acid sequence shown in SEQ ID NO: 1 can be arbitrarily produced, so as to select and use those having an excellent antibody titer.

Example 4

8 patients likely to have a perilymph fistula, who underwent the detection of the disease by the method of the present invention in the Examples 1 and 2 above, were also subjected to exploratory tympanotomy, the previously used method for differentiating perilymph fistulas (hereinafter referred to as "the conventional method" at times), so as to confirm whether or not the perilymph was leaked into the tympanic cavity. In addition, in all the cases, based on the assumption that there was a fistula, dehydrated fascia sections, which had been produced by compressing with gauze the fascia collected from the patients themselves, were placedon the inner ear windows (round window, oval window) and the fissura ante fenestram, and these sections were fixed with fibrin glue (Beriplast P, Aventis Pharma), so that the fistula was closed (hereinafter referred to as an "operative repair of fistulas" at times). Among various types of acute sensorineural hearingloss, the perilymph fistula is the only disease we can cure the hearingloss with the prompt surgical treatment and then the cure rate will be improved. Thus, with regard to these 8 patients, the results obtained by the method of the present invention, the results obtained by the conventional method, and the recovery of hearing by the operative repair of fistulas were compared and studied. As stated above, a sufficient explanation was given to the patients likely to have a perilymph fistula regarding the purpose of collecting a sample and the use of the sample for research purposes, and thus, the patients gave full informed consent for the collection of the specimens.

Before and after the operative repair of fistulas, an audiometrictest was carried out using an audiometer (AA-75 or AA-75N manufactured by Rion) in accordance with audiometry determined by the Japan Audiological Society. Evaluation was carried out with the mean value of the hearing levels of 5 frequencies, 250 Hz, 500 Hz, 1,000 Hz, 2,000 Hz, and 4,000 Hz. According to the criteria of hearing recovery determined by the research project team regarding acute profound sensorineural hearingloss, the Ministry of Health, Labour and Welfare, a case where the test value was improved to the same level as a normal ear or an ear before development of the disease, after the operation, was defined as "cured," a case where the mean value of the 5 frequencies was improved at a level of 30 decibels (dB) or more was defined as "significantly recovered," and a case where the mean value was improved at a level between 10 dB and 30 dB was defined as "recovered," and a case where the mean value was improved at a level of 10 dB or less was defined as "not changed." The results of the detection of perilymph fistulas in Examples 1 and 2 are shown in Tables 1 and 2. Moreover, the results are also shown in Table 3 to compare Examples 1 and 2 with the present example.

TABLE 3

|  | Method of the present invention | Leakage | Determination | Findings |
| --- | --- | --- | --- | --- |
| Suspected perilymph fistula | 1 | + | Not observed | Not changed | A case of profound hearingloss whose improvement was difficult |
|  | 2 | − | Not observed | Not changed |  |
|  | 3 | − | Observed | Not changed | Hearing deteriorated 1 year after the operation. As a result of MRI, the patient was diagnosed as acoustic neuroma. |
|  | 4 | − | Clearly observed | Cured |  |
|  | 5 | + | Observed | Cured |  |

TABLE 3-continued

| Method of the present invention | Leakage | Determination | Findings |
|---|---|---|---|
| 6 | + | Observed | Significantly recovered |
| 7 | + | Observed | Not changed | A case where it took a long time from the onset of the disease to the operation. |
| 8 | + | Observed | Significantly recovered |

As a result, in 5 cases out of the total 8 cases where patients were likely to have a perilymph fistula, the results obtained by the conventional method matched with the results obtained by the method of the present invention. The results did not match in 3 cases.

In these 3 cases where conflicting diagnosis were made, suspected perilymph fistula case 1 where no perilymph leakage was visible during the surgery but it was determined to be positive by the method of the present invention was a case of profound hearingloss, which was hardly improved by operation. Thus, hearing was not improved, but it was diagnosed as a perilymph fistula.

In addition, in suspected perilymph fistula case 3, one of the 2 cases where leakage of the perilymph was visible but it was determined to be negative by the method of the present invention, hearing further deteriorated 1 year after the operation. Thus, the possibility of other diseases was reviewed. As a result, it was confirmed by MRI (magnetic resonance imaging) that this patient suffered from acoustic neuroma. There is a possibility that a patient has other diseases, even with the facts that a patient is likely to have a perilymph fistula due to physiological findings and symptoms in accordance with the current criteria of diagnosis of the Heath, Labour and Welfare Ministry, that leakage of the perilymph from the oval window and the round window was confirmed by visual observation with a microscope during exploratory tympanotomy, and that it was diagnosed as a perilymph fistula. Further, such a patient was determined to be negative in the test performed by the method of the present invention. These results suggest the reliability of the present invention.

In suspected perilymph fistula case 4, it was determined that leakage of the perilymph was clearly observed. However, since a large amount of liquid that was clearly different from the common leakage of the perilymph was observed, there is a possibility that it was not leakage of the perilymph, but that a saline solution injected to collect the sample of the present invention was not sufficiently eliminated.

In suspected perilymph fistula case 7, leakage of the perilymph was observed, and further, it was determined to be positive by the present method. However, the hearing of the patient was not improved even after operative repair of fistulas. This may be because it took a long time, such as a time of period of 17 days, from the onset of the disease to the operation. Even in the case of a perilymph fistula, when it took a long time from the onset of the disease to the operation and the damage to the inner ear function has progressed, when the symptom is serious, when a patient is at an old age, or when complications occur, the hearing of the patient may not be improved in some cases even after undergoing the operation.

It was confirmed that 5 cases that were determined to be positive by the method of the present invention, among the total 8 suspected perilymph fistula cases, were all perilymph fistulas. It was also confirmed that 1 case out of the total 3 cases that was determined to be negative by the method of the present invention involved another disease. Accordingly, it can be said that if the sample collected from a patient is determined to be positive by the method of the present invention, the patient has a perilymph fistula.

INDUSTRIAL APPLICABILITY

The present invention provides a method for detecting perilymph fistulas, which is simple, reliable and low-invasive to the patients. According to the above method technique, a perilymph fistula can be objectively diagnosed without depending on the subjective judgment of the surgeon, which was impossible by the pervious methods. Thus, it becomes possible to substantially differentiate the perilymph fistula from other types of acute sensorineural hearingloss such as Meniere's disease or sudden deafness in the clinical site. This enables quick and adequate determination of treatment policy, and the cure rate can be significantly improved.

The present application claims priority from a Japanese Patent Application filed on Jun. 27, 2002 (Japanese Patent Application No. 2002-187479), and the disclosure of which is hereby incorporated by reference. In addition, all publications cited herein are also incorporated herein by reference.

The invention claimed is:

1. A method for detecting a perilymph fistula, which comprises detecting the existence of a p63 isoform of Cochlin, an N-terminal fragment of a p63 isoform of Cochlin, or a 16 kDa N-terminal fragment of Cochlin in body fluid existing in the middle ear with an antibody which recognizes an antigenic determinant contained in amino acids 36 to 127 of the amino acid, sequence shown in SEQ ID NO: 1; and using the detected existence of the p63 isoform of Cochlin the N-terminal fragment of a p63 isoform of Cochlin, or the 16 kDa N-terminal fragment of Cochlin as an indicator of a perilymph fistula.

2. The method according to claim 1, which comprises detecting the existence of a p63 isoform of Cochlin, an N-terminal fragment of a p63 isoform of Cochlin, or a 16 kDa N-terminal fragment of Cochlin in body fluid existing in the middle ear of a patient likely to have a perilymph fistula.

3. The method according to claim 1, wherein the antibody recognizes an antigenic determinant contained in a polypeptide consisting of the amino acid sequence shown in SEQ ID NO: 2, 5, 6, or 7.

* * * * *

UNITED STATES PATENT AND TRADEMARK OFFICE
CERTIFICATE OF CORRECTION

PATENT NO. : 7,863,005 B2
APPLICATION NO. : 10/517778
DATED : January 4, 2011
INVENTOR(S) : T. Ikezono et al.

It is certified that error appears in the above-identified patent and that said Letters Patent is hereby corrected as shown below:

On Cover Page, (75), line 3, of the printed patent, "Kanagawa, JP" should be changed to --Tokyo, JP--.

At column 37, line 33 (claim 1, line 8) of the printed patent, "," should be deleted after acid.

At column 37, line 35 (claim 1, line 10) of the printed patent, --,-- should be inserted after Cochlin.

Signed and Sealed this
Second Day of August, 2011

David J. Kappos
*Director of the United States Patent and Trademark Office*

SEQUENCE LISTING

```
<160> NUMBER OF SEQ ID NOS: 7

<210> SEQ ID NO 1
<211> LENGTH: 550
<212> TYPE: PRT
<213> ORGANISM: Homo sapiens
<220> FEATURE:
<221> NAME/KEY: Signal
```

<222> LOCATION: (1)..(24)

<400> SEQUENCE: 1

Met Ser Ala Ala Trp Ile Pro Ala Leu Gly Leu Gly Val Cys Leu Leu
1               5                   10                  15

Leu Leu Pro Gly Pro Ala Gly Ser Glu Gly Ala Ala Pro Ile Ala Ile
            20                  25                  30

Thr Cys Phe Thr Arg Gly Leu Asp Ile Arg Lys Glu Lys Ala Asp Val
        35                  40                  45

Leu Cys Pro Gly Gly Cys Pro Leu Glu Glu Phe Ser Val Tyr Gly Asn
    50                  55                  60

Ile Val Tyr Ala Ser Val Ser Ser Ile Cys Gly Ala Ala Val His Arg
65                  70                  75                  80

Gly Val Ile Ser Asn Ser Gly Pro Val Arg Val Tyr Ser Leu Pro
                85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
            115                 120                 125

Ser Thr Gln Glu Ala Thr Gly Gln Ala Val Ser Thr Ala His Pro Pro
130                 135                 140

Thr Gly Lys Arg Leu Lys Lys Thr Pro Glu Lys Lys Thr Gly Asn Lys
145                 150                 155                 160

Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
210                 215                 220

Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val
            260                 265                 270

Phe Ile Asp Gly Trp Pro Ser Asp Asp Ile Glu Glu Ala Gly Ile Val
        275                 280                 285

Ala Arg Glu Phe Gly Val Asn Val Phe Ile Val Ser Val Ala Lys Pro
290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350

His Glu Gln Met Met Cys Ser Lys Thr Cys Tyr Asn Ser Val Asn Ile
        355                 360                 365

Ala Phe Leu Ile Asp Gly Ser Ser Val Gly Asp Ser Asn Phe Arg
370                 375                 380

Leu Met Leu Glu Phe Val Ser Asn Ile Ala Lys Thr Phe Glu Ile Ser
385                 390                 395                 400

-continued

```
Asp Ile Gly Ala Lys Ile Ala Ala Val Gln Phe Thr Tyr Asp Gln Arg
                405                 410                 415

Thr Glu Phe Ser Phe Thr Asp Tyr Ser Thr Lys Glu Asn Val Leu Ala
            420                 425                 430

Val Ile Arg Asn Ile Arg Tyr Met Ser Gly Thr Ala Thr Gly Asp
        435                 440                 445

Ala Ile Ser Phe Thr Val Arg Asn Val Phe Gly Pro Ile Arg Glu Ser
    450                 455                 460

Pro Asn Lys Asn Phe Leu Val Ile Val Thr Asp Gly Gln Ser Tyr Asp
465                 470                 475                 480

Asp Val Gln Gly Pro Ala Ala Ala His Asp Ala Gly Ile Thr Ile
                485                 490                 495

Phe Ser Val Gly Val Ala Trp Ala Pro Leu Asp Asp Leu Lys Asp Met
            500                 505                 510

Ala Ser Lys Pro Lys Glu Ser His Ala Phe Phe Thr Arg Glu Phe Thr
        515                 520                 525

Gly Leu Glu Pro Ile Val Ser Asp Val Ile Arg Gly Ile Cys Arg Asp
    530                 535                 540

Phe Leu Glu Ser Gln Gln
545                 550

<210> SEQ ID NO 2
<211> LENGTH: 15
<212> TYPE: PRT
<213> ORGANISM: Homo sapiens

<400> SEQUENCE: 2

Thr Arg Gly Leu Asp Ile Arg Lys Glu Lys Ala Asp Val Leu Cys
1               5                   10                  15

<210> SEQ ID NO 3
<211> LENGTH: 15
<212> TYPE: PRT
<213> ORGANISM: Homo sapiens

<400> SEQUENCE: 3

Ala Val Ser Thr Ala His Pro Ala Thr Gly Lys Arg Leu Lys Lys
1               5                   10                  15

<210> SEQ ID NO 4
<211> LENGTH: 19
<212> TYPE: PRT
<213> ORGANISM: Homo sapiens

<400> SEQUENCE: 4

Lys Ala Asp Ile Ala Phe Leu Ile Asp Gly Ser Phe Asn Ile Gly Gln
1               5                   10                  15

Arg Arg Phe

<210> SEQ ID NO 5
<211> LENGTH: 21
<212> TYPE: PRT
<213> ORGANISM: Homo sapiens

<400> SEQUENCE: 5

Gly Asn Ile Val Tyr Ala Ser Val Ser Ser Ile Cys Gly Ala Ala Val
1               5                   10                  15

His Arg Gly Val Ile
                20
```

```
<210> SEQ ID NO 6
<211> LENGTH: 17
<212> TYPE: PRT
<213> ORGANISM: Homo sapiens

<400> SEQUENCE: 6

Leu Pro Gly Arg Glu Asn Tyr Ser Ser Val Asp Ala Asn Gly Ile Gln
1               5                   10                  15

Ser

<210> SEQ ID NO 7
<211> LENGTH: 14
<212> TYPE: PRT
<213> ORGANISM: Homo sapiens

<400> SEQUENCE: 7

Leu Ser Arg Trp Ser Ala Ser Phe Thr Val Thr Lys Gly Lys
1               5                   10
```